US009717685B2

(12) United States Patent
Shih et al.

(10) Patent No.: US 9,717,685 B2
(45) Date of Patent: Aug. 1, 2017

(54) LIPID-COATED NUCLEIC ACID NANOSTRUCTURES OF DEFINED SHAPE

(71) Applicant: President and Fellows of Harvard College, Cambridge, MA (US)

(72) Inventors: William M. Shih, Cambridge, MA (US); Steven Perrault, Toronto (CA)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/387,645

(22) PCT Filed: Mar. 13, 2013

(86) PCT No.: PCT/US2013/030765
§ 371 (c)(1),
(2) Date: Sep. 24, 2014

(87) PCT Pub. No.: WO2013/148186
PCT Pub. Date: Oct. 3, 2013

(65) Prior Publication Data
US 2015/0064233 A1    Mar. 5, 2015

Related U.S. Application Data

(60) Provisional application No. 61/615,740, filed on Mar. 26, 2012.

(51) Int. Cl.
| *A61K 9/127* | (2006.01) |
| *A61K 47/48* | (2006.01) |
| *A61K 9/00* | (2006.01) |
| *C12N 15/88* | (2006.01) |
| *B82Y 5/00* | (2011.01) |
| *B82Y 40/00* | (2011.01) |

(52) U.S. Cl.
CPC ............ *A61K 9/127* (2013.01); *A61K 9/0019* (2013.01); *A61K 9/0024* (2013.01); *A61K 9/1271* (2013.01); *A61K 47/48046* (2013.01); *A61K 47/48092* (2013.01); *A61K 47/48815* (2013.01); *B82Y 5/00* (2013.01); *C12N 15/88* (2013.01); *B82Y 40/00* (2013.01)

(58) Field of Classification Search
None
See application file for complete search history.

(56) References Cited

U.S. PATENT DOCUMENTS

| 7,842,793 B2 | 11/2010 | Rothemund | |
| 8,501,923 B2 * | 8/2013 | Rothemund | C12P 19/34 536/23.1 |
| 2009/0088372 A1 | 4/2009 | Roy et al. | |
| 2010/0216978 A1 | 8/2010 | Shih | |
| 2010/0324124 A1 | 12/2010 | Irvine et al. | |
| 2011/0275702 A1 | 11/2011 | Chang et al. | |
| 2011/0321183 A1 | 12/2011 | Ploegh et al. | |
| 2012/0282670 A1 | 11/2012 | Rossomando | |
| 2013/0230570 A1 | 9/2013 | Trogler et al. | |
| 2015/0064233 A1 | 3/2015 | Shih et al. | |

FOREIGN PATENT DOCUMENTS

| WO | WO 01/18015 A1 | 3/2001 |
| WO | WO 2012/142659 A1 | 10/2012 |
| WO | WO 2013/003555 A1 | 1/2013 |
| WO | WO 2013/054286 A1 | 4/2013 |
| WO | WO 2013/148186 A1 | 10/2013 |

OTHER PUBLICATIONS

Ko, et al. (2009) "Self-Assembling Micelle-like Nanoparticles Based on Phospholipid-Polyethyleneimine Conjugates for Systemic Gene Delivery", Journal of Controlled Release, 133(2): 132-38.*
Howarth, et al. (2006) "A monovalent streptavidin with a single femtomolar biotin binding stie", Nature Methods, 3(4): 267-73.*
Hook, et al. (Jul. 31, 2008) "Supported lipid bilayers, tethered lipid vesicles, and vesicle fusion investigated using gravimetric, plasmonic, and microscopy techniques", Biointerphases, 3(2): FA108-16.*
Banchelli et al., Phospholipid membranes decorated by cholesterol-based oligonucleotides as soft hybrid nanostructures. J Phys Chem B. Sep. 4, 2008;112(35):10942-52. doi: 10.1021/jp802415t. Epub Aug. 9, 2008.
Bellot et al., Recovery of intact DNA nanostructures after agarose gel-based separation. Nat Methods. Mar. 2011;8(3):192-4. doi:10.1038/nmeth0311-192.
Dietz et al., Folding DNA into twisted and curved nanoscale shapes. Science. Aug. 7, 2009;325(5941):725-30. doi: 10.1126/science.1174251.
Douglas et al., Rapid prototyping of 3D DNA-origami shapes with caDNAno. Nucleic Acids Res. Aug. 2009;37(15):5001-6. doi: 10.1093/nar/gkp436. Epub Jun. 16, 2009.
Douglas et al., Self-assembly of DNA into nanoscale three-dimensional shapes. Nature. May 21, 2009;459(7245):414-8. doi: 10.1038/nature08016.
Högberg et al., Folding DNA origami from a double-stranded source of scaffold. J Am Chem Soc. Jul. 8, 2009;131(26):9154-5. doi: 10.1021/ja902569x.
Ke et al., Multilayer DNA origami packed on a square lattice. J Am Chem Soc. Nov. 4, 2009;131(43):15903-8. doi: 10.1021/ja906381y.
Ko et al., Self-assembling micelle-like nanoparticles based on phospholipid-polyethyleneimine conjugates for systemic gene delivery. J Control Release. Jan. 19, 2009;133(2):132-8. doi:10.1016/j.jconrel.2008.09.079. Epub Oct. 7, 2008.
Langecker et al., Synthetic lipid membrane channels formed by designed DNA nanostructures. Science. Nov. 16, 2012;338(6109):932-6. doi: 10.1126/science.1225624.

(Continued)

*Primary Examiner* — Robert M Kelly
(74) *Attorney, Agent, or Firm* — Wolf, Greenfeld & Sacks, P.C.

(57) ABSTRACT

The invention provides nanoparticles containing a nucleic acid nanostructure, of defined shape and size, linked to a hydrophobic moiety and coated by lipids, compositions comprising the nanoparticles, and methods of producing and methods of using the nanoparticles.

31 Claims, 8 Drawing Sheets

(56) References Cited

OTHER PUBLICATIONS

Liedl et al., Self-assembly of three-dimensional prestressed tensegrity structures from DNA. Nat Nanotechnol. Jul. 2010;5(7):520-4. doi: 10.1038/nnano 2010.107. Epub Jun. 20, 2010.
Nikolov et al., Behavior of giant vesicles with anchored DNA molecules. Biophys J. Jun. 15, 2007;92(12):4356-68. Epub Mar. 23, 2007.
Pinheiro et al., Challenges and opportunities for structural DNA nanotechnology. Nat Nanotechnol. Nov. 6, 2011;6(12):763-72. doi:10.1038/nnano.2011.187.
Rothemund, Folding DNA to create nanoscale shapes and patterns. Nature. Mar. 16, 2006;440(7082):297-302.
Shih et al., A 1.7-kilobase single-stranded DNA that folds into a nanoscale octahedron. Nature. Feb. 12, 2004;427(6975):618-21.
Shih et al., Knitting complex weaves with DNA origami. Curr Opin Struct Biol. Jun. 2010;20(3):276-82. doi: 10.1016/j.sbi.2010.03.009. Epub Apr. 22, 2010.
Yoshina-Ishii et al., General method for modification of liposomes for encoded assembly on supported bilayers. J Am Chem Soc. Feb. 9, 2005;127(5):1356-7.
Jungmann et al., Isothermal assembly of DNA origami structures using denaturing agents. J Am Chem Soc. Aug. 6, 2008;130(31):10062-3. doi: 10.1021/ja8030196. Epub Jul. 10, 2008.
Shih, Biomolecular assembly: dynamic DNA. Nat Mater. Feb. 2008;7(2):98-100. doi: 10.1038/nmat2110.
U.S. Appl. No. 15/034,566, filed May 6, 2016, Pending.
U.S. Appl. No. 14/903,463, filed Jan. 7, 2016, Pending.
PCT/US2014/046251, Nov. 4, 2014, International Search Report and Written Opinion.
PCT/US2014/046251, Jan. 21, 2016, International Preliminary Report on Patentability.
PCT/US2014/064659, Feb. 13, 2015, International Search Report and Written Opinion.
PCT/US2014/064659, May 19, 2016, International Preliminary Report on Patentability.
Cecconi et al., Protein-DNA chimeras for single molecule mechanical folding studies with the optical tweezers. Eur Biophys J. Jul. 2008;37(6):729-38. doi: 10.1007/s00249-007-0247-y. Epub Jan. 9, 2008.
Chen et al., A general strategy for the evolution of bond-forming enzymes using yeast display.Proc Natl Acad Sci U S A. Jul. 12, 2011;108(28):11399-404. doi: 10.1073/pnas.1101046108. Epub Jun. 22, 2011.
Eskelinen et al., Controlling the formation of DNA origami structures with external signals. Small. Jul. 9, 2012;8(13):2016-20. doi: 10.1002/smll.201102697. Epub Apr. 17, 2012.
Gordon et al., Reactivity of biarylazacyclooctynones in copper-free click chemistry. J Am Chem Soc. Jun. 6, 2012;134(22):9199-208. doi: 10.1021/ja3000936. Epub May 24, 2012.
Halvorsen et al., Nanoengineering a single-molecule mechanical switch using DNA self-assembly. Nanotechnology. Dec. 9, 2011;22(49):494005. doi: 10.1088/0957-4484/22/49/494005. Epub Nov. 21, 2011.
Han et al., DNA origami with complex curvatures in three-dimensional space. Science. Apr. 15, 2011;332(6027):342-6. doi: 10.1126/science.1202998.
Jones et al., Nanomaterials. Programmable materials and the nature of the DNA bond. Science. Feb. 20, 2015;347(6224):1260901. doi:10.1126/science.1260901.
Kazmierczak et al., Cadherin 23 and protocadherin 15 interact to form tip-link filaments in sensory hair cells. Nature. Sep. 6, 2007;449(7158):87-91.
Linko et al., The enabled state of DNA nanotechnology. Curr Opin Biotechnol. Aug. 2013;24(4):555-61. doi: 10.1016/j.copbio.2013.02.001. Epub Apr. 6, 2013.
Martin, Functional Synthetic DNA Nanostructures. Dissertation. Technische Universität München, Laboratory for Biomolecular Nanotechnology. Filed on Mar. 12, 2013.
Niemeyer, The developments of semisynthetic DNA-protein conjugates. Trends Biotechnol. Sep. 2002;20(9):395-401.
Popp et al., Sortagging: a versatile method for protein labeling.Nat Chem Biol. Nov. 2007;3(11):707-8. Epub Sep. 23, 2007.
Saccà et al., Functionalization of DNA nanostructures with proteins. Chem Soc Rev. Dec. 2011;40(12):5910-21. doi: 10.1039/c1cs15212b. Epub Oct. 5, 2011.
Sotomayor et al., Structural determinants of cadherin-23 function in hearing and deafness. Neuron. Apr. 15, 2010;66(1):85-100. doi: 10.1016/j.neuron.2010.03.028.
Sotomayor et al., Structure of a force-conveying cadherin bond essential for inner-ear mechanotransduction. Nature. Dec. 6, 2012;492(7427):128-32. doi: 10.1038/nature11590. Epub Nov. 7, 2012.
Yang et al., Nanostructures as Programmable Biomolecular Scaffolds. Bioconjug Chem. Aug. 19, 2015;26(8):1381-95. doi:10.1021/acs.bioconjchem.5b00194. Epub May 22, 2015.
Zhang et al., Structural DNA nanotechnology: state of the art and future perspective. J Am Chem Soc. Aug. 13, 2014;136(32):11198-211. doi:10.1021/ja505101a. Epub Jul. 28, 2014.

\* cited by examiner

LIPID-COATED NUCLEIC ACID NANOSTRUCTURES OF DEFINED SHAPE

RELATED APPLICATIONS

This application is a national stage filing under 35 U.S.C. §371 of International Application No. PCT/US2013/030765 filed Mar. 13, 2013, which was published under PCT Article 21(2) in English, and which claims the benefit under 35 U.S.C. §119(e) of U.S. provisional application No. 61/615,740, filed Mar. 26, 2012, each of which is incorporated by reference herein in its entirety.

GOVERNMENT SUPPORT

This invention was made with government support under 1DP2 OD004641-01 awarded by National Institutes of Health. The Government has certain rights in the invention.

FIELD OF INVENTION

Aspects and embodiments of the invention relate to the field of structural nucleic acid nanotechnology.

BACKGROUND OF INVENTION

Structural nucleic acid nanotechnology allows for production of two- and three-dimensional nanometer-scale structures based on nucleic acids (e.g., DNA). The structures are produced, for example, through predictable hybridization of DNA into its double-stranded form. In some instances, structures may be produced (referred to herein as "folded") using a very long strand, termed a "scaffold" strand, and a number of short strands, referred to as either oligonucleotides or "staple" strands. Each staple strand binds the scaffold strand at two or more non-contiguous regions, resulting in various, typically predictable, shapes. Nucleic acid structures may also be produced using staple strands in the absence of a scaffold strand. Depending on the size of the resulting shape, different numbers of strands may be used, ranging from as few as three or four strands to many hundreds or even thousands of strands to produce a stable nucleic acid nano structure.

Nonetheless, in uncontrolled, undefined environments (e.g., in vivo), nucleic acid structures may be unstable as a result of their susceptibility to degradation through a number of different mechanisms, including but not limited to nuclease degradation, depletion of cations, and sensitivity to pH.

SUMMARY OF INVENTION

The invention provides generally, inter alia, a nanoparticle containing a nucleic acid nano structure core linked to and typically covered by a lipid shell (such as a lipid bilayer shell). The nucleic acid nanostructure core is typically a defined two- or three-dimensional shape. According to some aspects of the invention, the nanostructure core is linked to a hydrophobic moiety and it is covered by a lipid bilayer that conforms in shape to the nucleic acid nanostructure core. The hydrophobic moiety may be conjugated to a nucleic acid, such as an oligonucleotide, that is bound to the nanostructure core. The hydrophobic moiety is able to interact with, for example, other hydrophobic moieties such as but not limited to a lipid bilayer that envelops the nano structure core.

Thus, in one aspect, the invention provides a shaped nanoparticle having a nucleic acid nanostructure core and a lipid coating, wherein the nucleic acid nanostructure is attached to a hydrophobic moiety, and wherein the hydrophobic moiety is in contact with the lipid coating. The hydrophobic moiety may be positioned within a layer of the lipid bilayer, or it may extend through both layers of the lipid bilayer.

In another aspect, the invention provides a shaped nanoparticle having a nucleic acid nanostructure core and a lipid coating, wherein the nucleic acid nanostructure is attached to a oligonucleotide conjugate comprising a hydrophobic moiety, and wherein the hydrophobic moiety is in contact with the lipid coating. The oligonucleotide may be completely or partially single-stranded.

In yet another aspect, the invention provides a composition comprising any one of the nanoparticles described herein. In some embodiments, a composition may comprise a carrier or excipient.

In still another aspect, the invention provides (a) a single-stranded "scaffold" nucleic acid hybridized to a plurality of short single-stranded "staple" nucleic acids, wherein the short nucleic acids are hybridized to two or more non-contiguous single-stranded regions (or sequences) in the single-stranded scaffold nucleic acid, thereby forming a nucleic acid nanostructure; (b) a plurality of oligonucleotide conjugates attached to the nucleic acid nanostructure, each conjugate comprised of a hydrophobic moiety covalently attached to a single-stranded oligonucleotide; and (c) a lipid bilayer exterior to the nucleic acid nanostructure, wherein the hydrophobic moiety is in contact with the lipid bilayer. In some embodiments, the lipid bilayer does not comprise cationic lipids.

In some embodiments, the oligonucleotide conjugates are attached to the nucleic acid nanostructure via hybridization to single-stranded nucleic acid handles.

In another aspect, the invention provides a composition comprising (a) a plurality of short single-stranded nucleic acids assembled into a defined shape to form a nucleic acid nanostructure; (b) a plurality of oligonucleotide conjugates attached to the nucleic acid nanostructure, each conjugate comprised of a hydrophobic moiety covalently attached to a single-stranded oligonucleotide; and (c) a lipid bilayer exterior to the nucleic acid nanostructure, and wherein the hydrophobic moiety is in contact with the lipid bilayer. In some embodiments, the lipid bilayer does not comprise cationic lipids. Depending on the embodiments, the overall charge of the lipid bilayer is negative, positive or neutral.

In yet another aspect, the invention provides a composition comprising a nanoparticle having a nucleic acid nanostructure core and a lipid bilayer coating, wherein the nucleic acid nanostructure is attached to (and/or presents) a single-stranded nucleic acid handle, wherein the handle is hybridized to a single-stranded oligonucleotide conjugate that is covalently linked to a hydrophobic moiety, and wherein the hydrophobic moiety is in contact with the lipid coating.

In various aspects, the invention provides a method of producing any one of the nanoparticles described herein, the method comprising: (a) combining a nucleic acid nanostructure having a single-stranded nucleic acid handle, and a complementary single-stranded oligonucleotide conjugate that comprises a hydrophobic moiety at one end of the oligonucleotide, and incubating the combination under conditions that permit complementary base pair annealing between the single-stranded nucleic acid handle and the single-stranded oligonucleotide conjugate, thereby forming a nucleic acid nanostructure linked to a hydrophobic moiety; and (b) combining the nucleic acid nanostructure linked to the hydrophobic moiety with lipids to produce the nanoparticle. In some embodiments, a method may further comprise combining the components in (a) with a surfactant. In some embodiments, a method may further comprise dialysis to remove the surfactant.

In some embodiments, the method further comprises isolating the nanoparticle. In some embodiments, the nanoparticle is isolated by dialysis. In some embodiments, the isolation of the nanoparticle comprises DNase digestion of nanostructures not coated with lipid bilayers. In some embodiments, the method further comprises purifying the nanoparticle. In some embodiments, the nanoparticle is purified by density gradient centrifugation. Other purification means may be used.

In some embodiments, the method comprises loading a purified nanoparticle with a therapeutic agent, a prophylactic agent, or a diagnostic agent. An agent may be loaded by combining the nanoparticle with the agent under conditions that permit attachment of the agent to the hydrophobic moiety. In some embodiments, an agent may be loaded by passive capture within the volume encapsulated by the lipid bilayer, or by coupling the agent to a single-stranded oligonucleotide complementary to single-stranded handles present on the nanostructure, and then by annealing the complementary strands.

In another aspect, the invention provides a method comprising administering to a subject any one of the nanoparticles or any one of the nanoparticle-containing compositions described herein.

In yet another aspect, the invention provides a method of treating or preventing a disease or disorder in a subject comprising administering to a subject in need thereof an effective amount of any one of the nanoparticles or any one of the nanoparticle-containing compositions provided herein, wherein the nanoparticle comprises a therapeutic agent or a prophylactic agent, thereby respectively treating or preventing the disease or disorder.

In yet another aspect, the invention provides a method of detecting a biomarker, disease, or disorder in a subject comprising administering to a subject in need thereof an effective amount of any one of the nanoparticles or any one of the nanoparticle-containing compositions provided herein, wherein the nanoparticle comprises a contrast agent and is formulated to provide an effective signal-over-noise for diagnostic detection purposes.

In still another aspect, the invention provides a kit comprising any one of the nanoparticles described herein and instructions for in vitro or in vivo use of the nanoparticle, including for example administration to a subject.

In a further aspect, the invention provides a kit comprising components for assembling any one of the nanoparticles described herein and instructions for assembling the nanoparticle. In some embodiments, the components of a kit may be selected from the group consisting of scaffold nucleic acids, staple oligonucleotides, single-stranded nucleic acid handles, single-stranded oligonucleotide conjugates, lipids, surfactant, and combinations thereof.

Various embodiments of the invention apply equally to the afore-mentioned aspects and embodiments. Such embodiments are recited below.

In some embodiments, the oligonucleotide conjugate comprises a hydrophobic moiety conjugated to an end of an oligonucleotide. In some embodiments, the oligonucleotide conjugate comprises a hydrophobic moiety conjugated to an internal region of the oligonucleotide. In some embodiments, the oligonucleotide of the conjugate is wholly single-stranded. In some embodiment, the oligonucleotide of the conjugate is partially single-stranded. Thus, in some embodiments, the oligonucleotide is at least partially double-stranded. In some embodiments, two or more hydrophobic moieties may be conjugated to the oligonucleotide. The hydrophobic moiety may be covalently or non-covalently conjugated to the oligonucleotide. In some embodiments, the hydrophobic moiety is a lipid, a peptide, or a surfactant.

The invention further contemplates use of a hydrophobic moiety coupled to a protein, peptide, metal or oligonucleotide that can interact with features on the nucleic acid nanostructure, thereby attaching the hydrophobic moiety to the nucleic acid nanostructure. In some embodiments, a binding pair such as biotin and streptavidin are used to attach the hydrophobic moiety directly to the nucleic acid nanostructure. It is to be understood that such conjugation means can be used in the various aspects and embodiments described herein.

In some embodiments, the lipid coating may be a lipid bilayer having an interior layer, a transmembrane region, and an exterior layer.

In some embodiments, the hydrophobic moiety may be positioned within one layer of the lipid bilayer. In some embodiments, the hydrophobic moiety may extend through both layers of the lipid bilayer, thereby providing a transmembrane moiety that extends from the interior to the exterior of the lipid bilayer. In some embodiments, the hydrophobic moiety is conjugated to another moiety that may be positioned exterior to the lipid bilayer. Such a moiety may be an agent such as a therapeutic, prophylactic or diagnostic agent, or it may be a universal binding partner that facilitates the binding of such agents as well as other agents.

In some embodiments, the oligonucleotide conjugate may be hybridized to the nucleic acid nanostructure. In some embodiments, the oligonucleotide conjugate may be hybridized to a single-stranded nucleic acid handle that is attached to the nucleic acid nanostructure. The single-stranded nucleic acid handle may be attached covalently or non-covalently to the nucleic acid nanostructure. In some embodiments, the single-stranded nucleic acid handle may be attached to the nucleic acid nanostructure by hybridization. In some embodiments, the single-stranded nucleic acid handle may be attached to the nucleic acid nanostructure through a binding pair. In some instances, the binding pair is biotin and streptavidin. In some embodiments, the single-stranded nucleic acid handle may be covalently attached to the nucleic acid nanostructure.

In some embodiments, the lipid coating may be heterogeneous. In some embodiments, the lipid coating may comprise a phospholipid, an aminolipid, a sphingolipid, or a combination thereof. In some embodiments, the lipid coating may comprise cholesterol, sphingomyelin, cardiolipin, or a combination thereof. In some embodiments, the lipid coating may comprise a neutral lipid, which may be uncharged or zwitterionic. In some embodiments, the lipid coating may not comprise cationic lipids. In some embodiments, the lipid coating may have an overall neutral or negative charge. In some embodiments, the lipid coating may have an overall neutral charge.

In some embodiments, the shape of the lipid coating may be substantially the same as the shape of the nucleic acid nanostructure. In some embodiments, the nucleic acid nanostructure is a defined shape selected from the group consisting of a hemi-sphere, a cube, a cuboidal, a tetrahedron, a cylinder, a cone, an octahedron, a prism, a sphere, a pyramid, a dodecahedron, a tube, an irregular shape, and an abstract shape. In some embodiments, the volume of the nanoparticle is substantially similar to the volume of the nanostructure.

In some embodiments, the nanoparticle has a cross section length of less than 1000 nanometers. In certain embodiments, the nanoparticle has a cross section length of greater than 1000 nanometers.

In some embodiments, the nanoparticles further comprise an agent. In some embodiments, the agent may be attached to a hydrophobic moiety that is linked to the nucleic acid nanostructure. In some embodiments, the agent may be a therapeutic agent, a prophylactic agent, or a diagnostic agent. In some embodiments, a nanoparticle may not comprise an agent.

DETAILED DESCRIPTION OF INVENTION

Figure 1A:
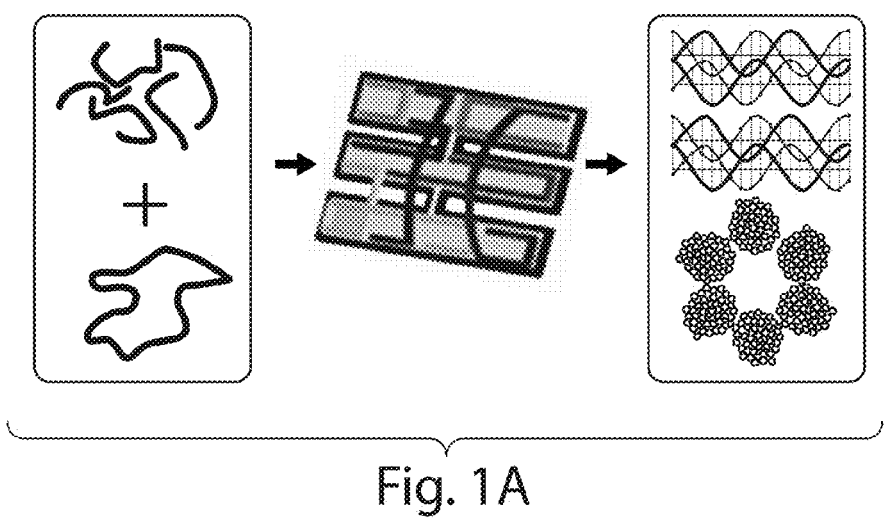
FIG. 1: Structural nucleic acid nanotechnology. (A) Schematic showing the concept of structural nucleic acid nanotechnology. In this case, a long circular single-stranded DNA is mixed with a large number of shorter synthetic oligonucleotides. Base-pair complementarity causes hybridization of the short strands to the longer strand, thereby "folding" the longer strand into a target shape. (B) Representative 2-dimensional structures (adapted from Rothmund, P. W. K. *Nature* 440 (7082): 297-302 (2006))). (C) Representative 3-dimensional structures (adapted from Douglas, S. M. et al. *Nature* 459, 414-418 (2009)), imaged using transmission electron microscopy.
Figure 1B:
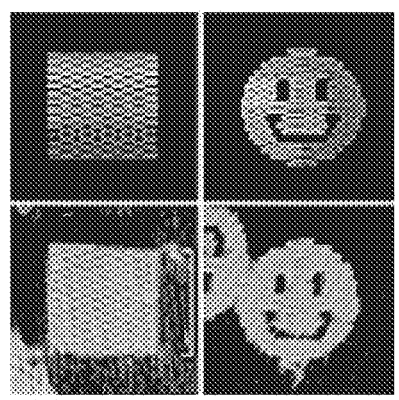
Figure 1C:
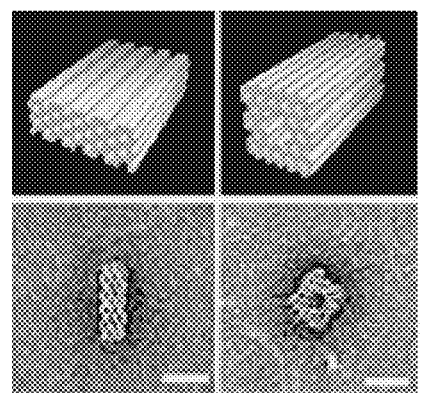
Figure 2:
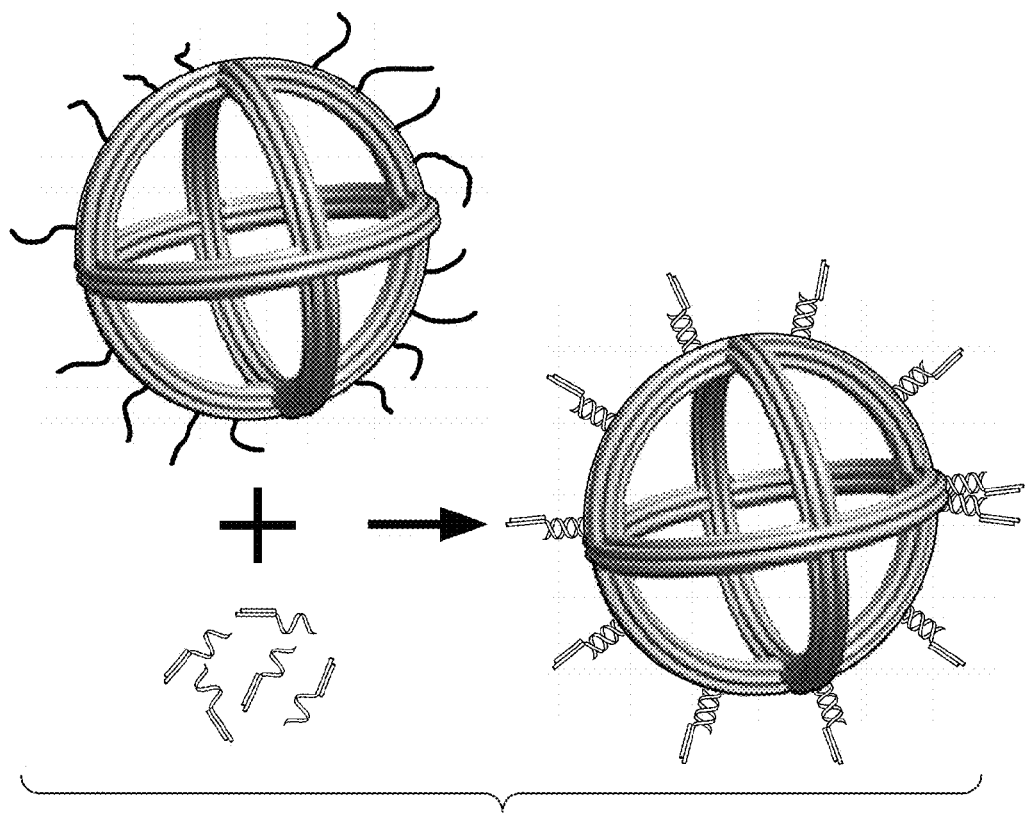
FIG. 2: Schematic showing annealing of hydrophobic moieties to a folded nanostructure. Purified nanostructures are mixed with oligonucleotide conjugates. Such conjugates are comprised of hydrophobic moieties attached to single-stranded oligonucleotides. The single-stranded oligonucleotides of the conjugates may be complementary to single-stranded oligonucleotide "handles" on the nanostructure. Hybridization of the two single-stranded oligonucleotides to each other results in attachment of the hydrophobic moieties to the nanostructure. In some instances, the hydrophobic moieties are prevented from aggregating by the presence of a surfactant at a concentration above its critical micelle concentration.
Figure 3:
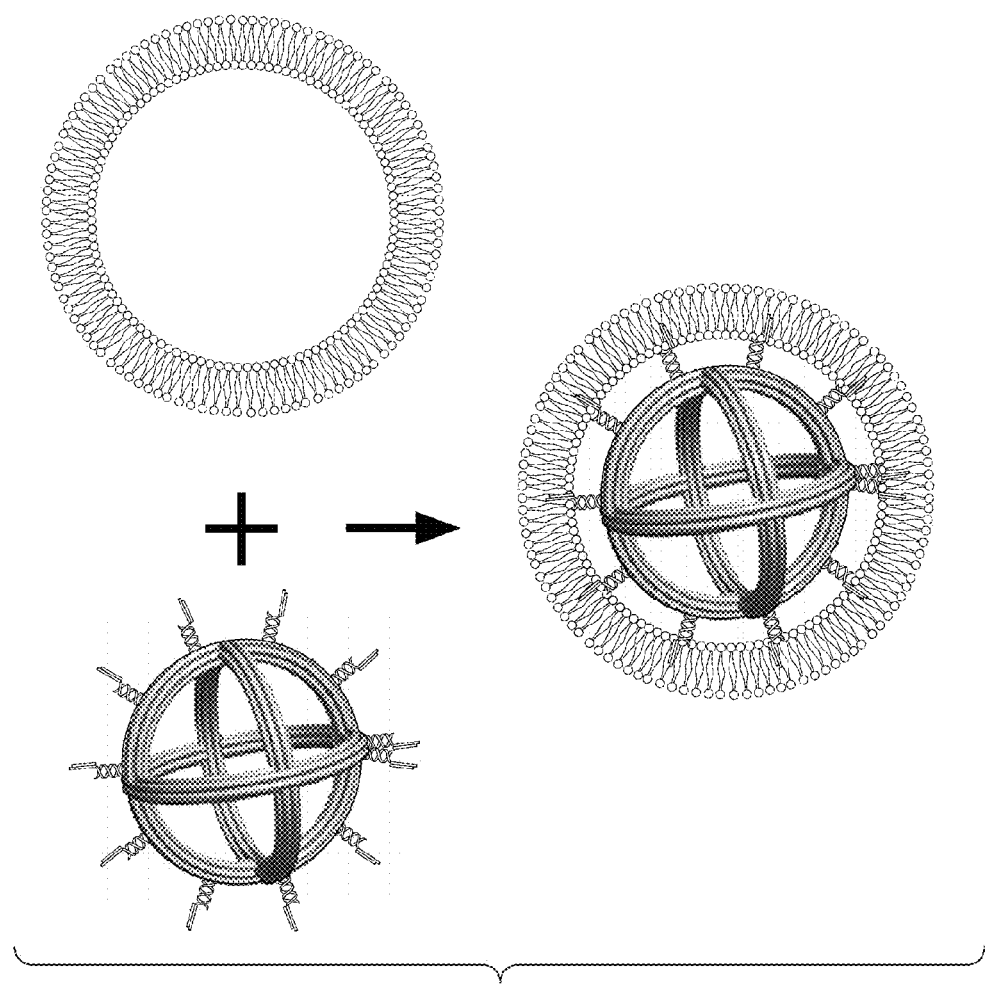
FIG. 3: Schematic showing lipid coating. The nanostructures with hydrophobic moieties are mixed with pre-formed lipid structures. Dialysis slowly removes the surfactant, driving interaction between the lipid structures and hydrophobic moieties. The lipids assemble around the DNA nanostructures, thereby partially or completely enveloping the nanostructure. In this example, the hydrophobic moieties are shown in the transmembrane (or hydrophobic) region of a lipid bilayer coating.
Figure 4A:
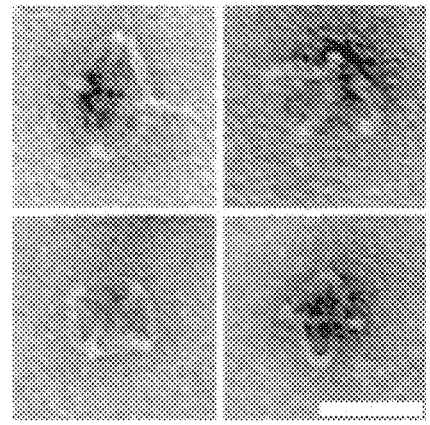
FIG. 4: Coating of octahedron DNA nanostructures. (A) Images obtained by transmission electron microscopy and negative staining of octahedron DNA nanostructures prior to lipid coating shows their geometry to be as expected. (B) Schematic showing assembly of the lipid bilayer around the structure. (C) Images obtained by transmission electron microscopy show the octahedron DNA nanostructures inside of and tightly-wrapped by lipid bilayers.
Figure 4B:
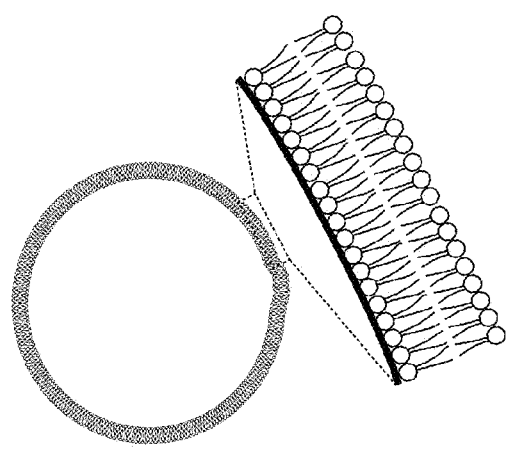
Figure 4C:
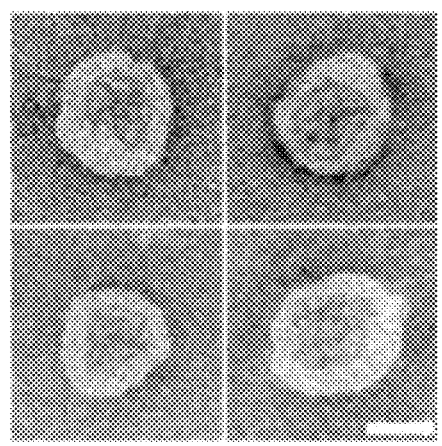
Figure 5:
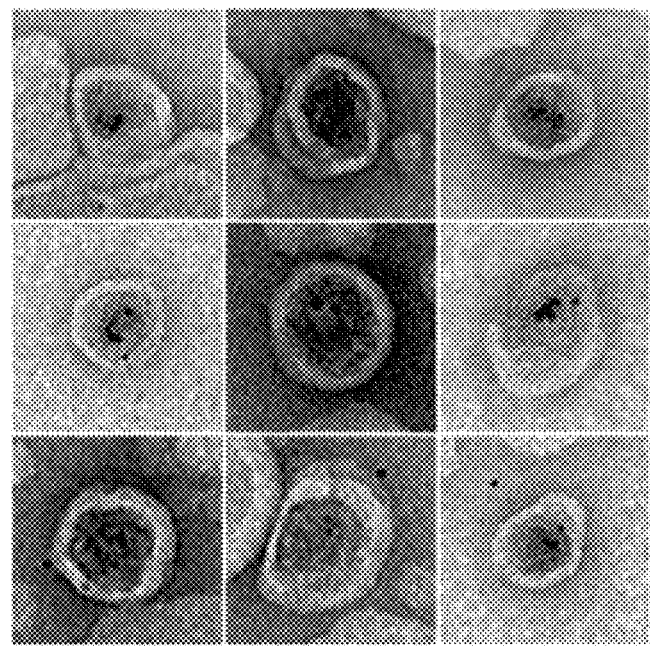
FIG. 5: Examples of coated DNA nanostructures. Octahedron DNA nanostructures were decorated with 5 nm gold nanoparticles (dark points) prior to coating. The nanostructures are coated by lipid bilayers.
Figure 6:
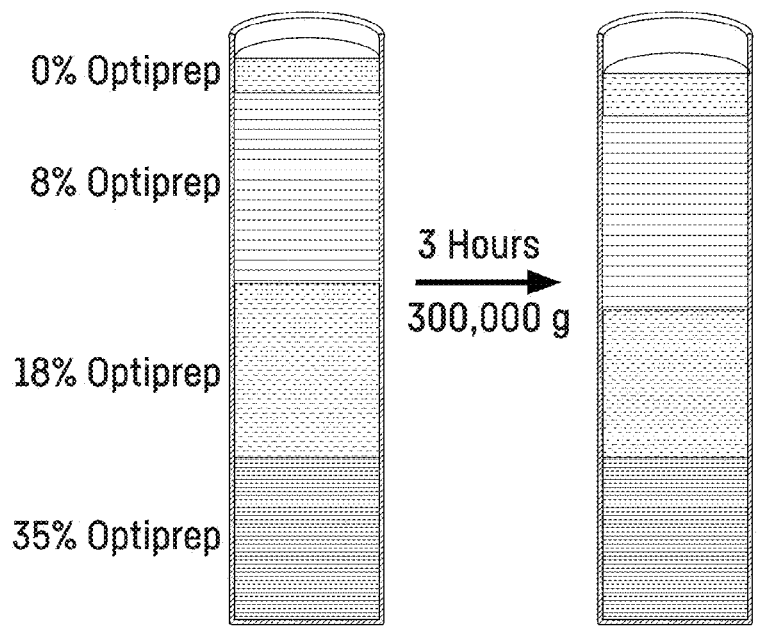
FIG. 6: Equilibrium density gradient centrifugation. OptiPrep™ density gradient medium is used to create a step-wise density gradient in an ultracentrifugation tube. In this case, sample is included in the most dense fraction, although it can be included in other fractions. Centrifugation for 3 hours at 300,000×g separates the sample according to density.
Figure 7:
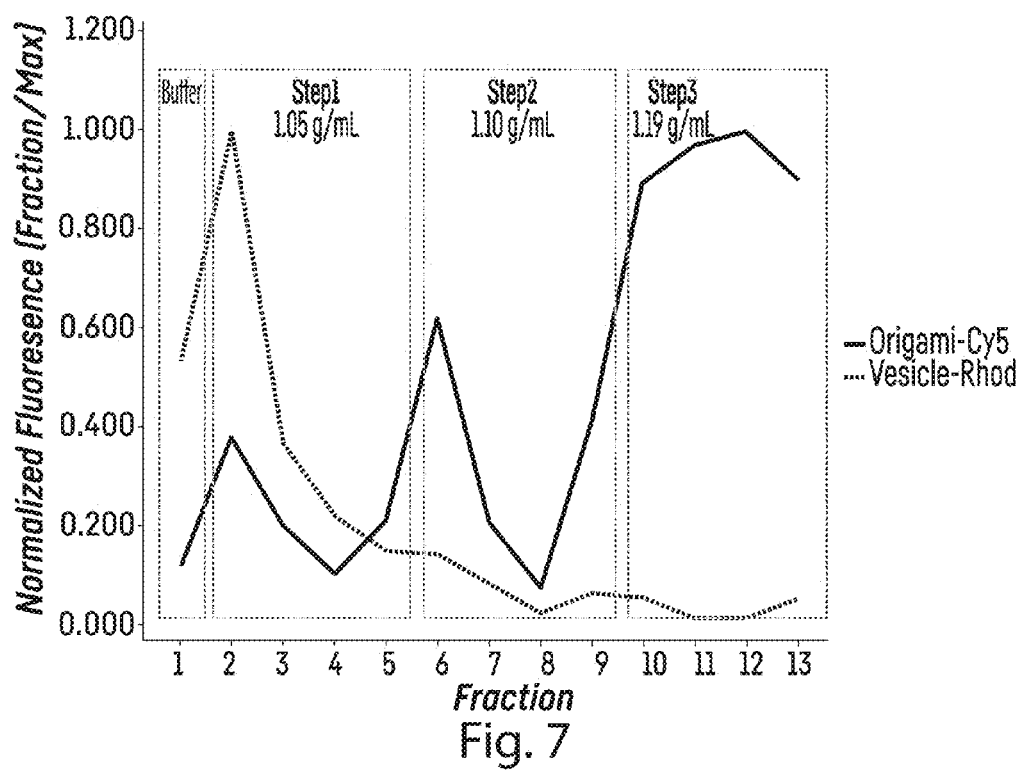
FIG. 7: Analysis of Density Gradient Centrifugation. The empty lipid structures and coated DNA nanostructures can be labeled with a fluorescent agent, allowing for analysis of density gradient centrifugation by fluorescence intensity of the two products. Most of the empty lipid structure fraction reaches equilibrium above the 1.05 g/mL step (gray line). The primary coated DNA nanostructure product reaches equilibrium above the 1.10 g/mL step (black line). Excess fluorophore not associated with the DNA nanostructure remains in the highest density fraction (1.15 g/mL).

The invention provides, in part, methods for protecting a two- or three-dimensional nucleic acid nanostructure from degradation by covering the nanostructure within a lipid (such as a lipid bilayer) coating.

The nucleic acid nanostructure is attached to a hydrophobic moiety (e.g., a lipid, a surfactant, a peptide, a protein, and/or other hydrophobic entity) through a variety of mechanisms. The hydrophobic moiety can be attached to a single-stranded oligonucleotide, thereby forming an "oligonucleotide conjugate," which hybridizes to a complementary region on the nucleic acid nanostructure. The hydrophobic moiety may be attached at and/or between the ends of the oligonucleotide. Such attachment may be covalent or non-covalent. Each conjugate may comprise one, two or more hydrophobic moieties. In some instances, the single-stranded oligonucleotide is complementary to and binds to a single-stranded nucleic acid strand present in the nanostructure, or is complementary to and binds to an intermediate single-stranded nucleic acid "handle" attached to the nanostructure. The nucleic acid handle may be attached to the nucleic acid nanostructure through intermediary molecules, for example, molecules such as but not limited to biotin/streptavidin, or through direct covalent attachment to nucleic acid strands contributing to the nanostructure.

The nanostructure may be attached to a hydrophobic moiety through the use of a binding pair, one member of which is attached to the nanostructure and one member of which is attached to the hydrophobic moiety. Examples of binding pairs include biotin-avidin, antigen-antibody or antibody fragment, ligand-receptor, etc.

The nucleic acid nanostructure with attached hydrophobic moieties is mixed with anionic, cationic, or neutral liposomes, and the hydrophobic moieties drive the interaction between the nucleic acid nanostructure and the lipids, causing wrapping of the lipids around the nanostructure to produce what is referred to herein as a nanoparticle, or a shaped nanoparticle.

Thus, the invention provides, inter alia, methods of producing a nanoparticle containing a two- or three-dimensional nucleic acid nanostructure that is linked to a hydrophobic moiety and is coated by lipids, the nanoparticles themselves as well as compositions comprising such nanoparticles, and methods of using such nanoparticles.

Nanoparticles

As used herein, "nanoparticle" or "shaped nanoparticle" refers to any partially or wholly lipid-coated nucleic acid nanostructure having a cross-section length in the range of 1 to 1000 nanometers (nm) (i.e., 1 micron). As used herein, cross-section length refers to the measurement of the longest cross-section length of the nanoparticle (e.g., the longest distance that can be measured between two points of a cross-section of the nanoparticle). In some instances, such particles will have a cross-section length in the range of 10 nm to 50 nm, 50 to 1000 nm, 50 to 900 nm, 50 to 800 nm, 50 to 700 nm, 50 to 600 nm, 50 to 500 nm, 50 to 400 nm, 50 to 300 nm, 50 to 200 nanometers, and/or 50 to 100 nm. The lower end of these ranges may alternatively be about 100 nm. In some instances, the particles will have a cross-section length of greater than 1 micron. The size of the nanoparticle is therefore predetermined and controlled as is the size of its nanostructure core, discussed below.

A nanoparticle typically has a defined, predetermined shape such as a sheet, a tube, a geometric shape, an irregular shape, or an abstract shape, based on the shape of its nucleic acid nanostructure core, as described below in more detail. A shaped nanoparticle may be and typically is a shape corresponding to its two- or three-dimensional nucleic acid nanostructure core. Though, in some embodiments, the shape of a nanoparticle may not correspond to its nanostructure core. The shape of the nanoparticle is therefore predetermined and controlled as is the shape of its nanostructure core, discussed below.

A nanoparticle comprises a two- or three-dimensional nucleic acid nanostructure core. The nucleic acid nanostructure core may be formed by hybridizing a (relatively) long nucleic acid strand (e.g., >1000 nucleotides in length) to a plurality of shorter oligonucleotides (e.g., <100 nucleotides in length) wherein each of the shorter oligonucleotides hybridize to two or more specific non-contiguous regions of the longer nucleic acid strand of nucleotides. The longer strand may be referred to as a scaffold strand, and the shorter strands may be referred to as staple strands. Alternatively, the nucleic acid nanostructure core may be produced by the assembly of a number of oligonucleotides, in the absence of the longer nucleic acid strand. The resultant nucleic acid structure retains its shape through nucleic acid hybridization (e.g., complementary Watson-Crick nucleotide base-pairing). Crosslinking within the nanostructure core may or may not be used in addition.

A nanoparticle comprises a protective coating. The coating may be composed of only lipids or it may comprise non-lipid moieties such as surfactants, peptides, and other hydrophobic or amphipathic molecules. The coating may be homogeneous (e.g., comprised of a single moiety) or it may be heterogeneous (e.g., comprised of a mixture of moieties). As an example, a lipid coating may be comprised of a single lipid species or it may be comprised of a two or more lipid species. Such lipid species may include neutral lipids and/or anionic lipids in varying molar ratios. Lipid species may also include, in some instance, cationic lipids.

The invention further provides populations (or pluralities) of the nanoparticles and populations (or pluralities) of the nanostructures that form their cores. Such populations may be relatively homogeneous or monodisperse. In some embodiments, at least 25%, at least 50%, at least 75%, or more of the nanoparticles (or nanostructures, as the case may be) in the population are of the same shape and same size. In some embodiments, the range of relative nanoparticle (or nanostructure) size may be from 75% to 125%, or 80% to 120%, or 90% to 110%, or 95% to 105%, wherein 100% represents the more common size of nanoparticle (or nanostructure) in the population or the predetermined size of nanoparticle (or nanostructure).

Nucleic Acid Nanostructures

As described herein, the core of a nanoparticle is a nucleic acid nanostructure, such as for example a DNA nanostructure. The nanostructure may be formed using any nucleic acid folding or hybridization methodology. One such methodology is DNA origami (Rothmund, P. W. K. (2006)). In a DNA origami approach, a nanostructure is produced by the folding of a longer "scaffold" nucleic acid strand through its hybridization to a plurality of shorter "staple" oligonucleotides, each of which hybridize to two or more non-contiguous regions within the scaffold strand. In some embodiments, a scaffold strand is at least 100 nucleotides in length. In some embodiments, a scaffold strand is at least 500, at least 1000, at least 2000, at least 3000, at least 4000, at least 5000, at least 6000, at least 7000, or at least 8000 nucleotides in length. The scaffold strand may be naturally or non-naturally occurring. Staple strands are typically less than 100 nucleotides in length; however, they may be longer or shorter depending on the application and depending upon the length of the scaffold strand. In some embodiments, a staple strand may be about 15 to about 100 nucleotides in length. In some embodiments the staple strand is about 25 to about 50 nucleotides in length.

In some embodiments, a nucleic acid nanostructure may be assembled in the absence of a scaffold strand (e.g., a scaffold-free structure). For example, a number of oligonucleotides (e.g., <200 nucleotides or less than 100 nucleotides in length) may be assembled to form a nucleic acid nanostructure.

Other methods for assembling nucleic acid nanostructures are known in the art, any one of which may be used herein. Such methods are described by, for example, Bellot G. et al., *Nature Methods*, 8: 192-194 (2011); Liedl T. et al., *Nature Nanotechnology*, 5: 520-524 (2010); Shih W. M. et al., *Curr. Opin. Struct. Biol.*, 20: 276-282 (2010); Ke Y. et al., *J. Am. Chem. Soc.*, 131: 15903-08 (2009); Dietz H. et al., *Science*, 325: 725-30 (2009); Hogberg B. et al., *J. Am. Chem. Soc.*, 131: 9154-55 (2009); Douglas S. M. et al., *Nature*, 459: 414-418 (2009); Jungmann R. et al., *J. Am. Chem. Soc.*, 130: 10062-63 (2008); Shih W. M., *Nature Materials*, 7: 98-100 (2008); and Shih W. M., *Nature*, 427: 618-21 (2004), each of which is incorporated herein by reference in its entirety.

A nucleic acid nanostructure may be assembled into one of many defined and predetermined shapes including without limitation a hemi-sphere, a cube, a cuboidal, a tetrahedron, a cylinder, a cone, an octahedron, a prism, a sphere, a pyramid, a dodecahedron, a tube, an irregular shape, and an abstract shape. The nanostructure may be have a void volume (i.e., it may be partially or wholly hollow). In some embodiments, the void volume may be at least 25%, at least 50%, at least 75%, at least 85%, at least 90%, or more of the volume of the nanostructure. Thus in some embodiments, the nanostructure and thus the nanoparticle does not comprise a solid core. In some embodiments, the nucleic acid nanostructure is not circular or near circular in shape. In some embodiments, the nucleic acid nanostructure is not a solid core sphere. Depending on the intended use of the shaped nanoparticle, the nanostructure may be assembled into a shape as simple as a two-dimensional sheet or as complex as a three-dimensional lattice.

In some embodiments, a nucleic acid nanostructure comprises a short, partially or wholly single-stranded nucleic acid "handle". One or more such handles may be attached to the nanostructure. In some embodiments, a handle is used as an intermediary to attach an oligonucleotide conjugate to the nanostructure. The length of a single-stranded nucleic acid handle may vary. In some embodiments, the handle (or at least the single-stranded region of the handle) may be about 15 to about 50 nucleotides in length. In some embodiments, a handle may be about 15, about 20, about 25, about 30, about 35, about 40, or about 50 nucleotides in length. Depending on the application, a single-stranded nucleic acid handle may be greater than 50 nucleotides in length. The handle may be attached to the nucleic acid nanostructure in a covalent or non-covalent manner. As a non-limiting example, it may be attached non-covalently to the nanostructure using a binding pair such as a biotin and avidin/streptavidin binding pair. Other binding pairs will be apparent to those of ordinary skill in the art and may be used for attachment, including high affinity protein/protein binding pairs such as antibody/antigen and ligand/receptor binding pairs.

In some embodiments, the hydrophobic moiety can be attached to the nucleic acid nanostructure without being conjugated to an intermediate oligonucleotide (e.g., an oligonucleotide that is not contributing to the structural integrity of the nanostructure). In such embodiments, the hydrophobic moiety can be attached to the nucleic acid nanostructure via a binding pair such as a biotin and avidin/streptavidin binding pair.

Oligonucleotide-Hydrophobic Moiety Conjugates

The nanoparticles of the invention comprise an oligonucleotide conjugate that bridges the nanostructure core and the polymer coating. The conjugate may facilitate the formation of a lipid bilayer coating around the nanostructure core and/or it may stabilize the coating. An "oligonucleotide conjugate" comprises a partially or wholly single-stranded oligonucleotide and a hydrophobic moiety attached to the oligonucleotide. The conjugate may comprise any hydrophobic moiety designed to interact with the lipid bilayer and with the nanostructure in a manner that assembles the lipid bilayer to the nanostructure.

The oligonucleotide may be about 15 to about 50 nucleotides in length. In some embodiments, the oligonucleotide may be about 15, about 20, about 25, about 30, about 35, about 40, or about 50 nucleotides in length. Depending on the application, the oligonucleotide may be greater than 50 nucleotides in length. The oligonucleotide may be complementary to an accessible single-stranded region of the oligonucleotide handle described above, or it may be complementary to an accessible single-stranded nucleotide region of the nucleic acid nanostructure. Thus, in some embodiments, an oligonucleotide conjugate is hybridized directly to the nanostructure, and in some embodiments, it is hybridized to an oligonucleotide handle that has been attached, covalently or non-covalently, to the nanostructure.

The hydrophobic moiety may be attached to an end region of the oligonucleotide (i.e., a 5' or a 3' end) and/or it may be attached to an internal region of the oligonucleotide (i.e., a region between the 5' and 3' ends). Each oligonucleotide may comprise a single hydrophobic moiety or a plurality of hydrophobic moieties. Such attachment may be accomplished during the synthesis of the oligonucleotide or following synthesis of the oligonucleotide. The hydrophobic moiety may be attached to the oligonucleotide in a covalent or a non-covalent manner. Examples of hydrophobic moieties that may be used herein include without limitation lipids, surfactants, peptides, proteins, synthetic macromolecules, and the like.

In instances where the nanoparticle has a lipid bilayer coating, the hydrophobic moiety may extend from the nanostructure core into the interior of the lipid bilayer (also referred to herein as the "transmembrane" region). The hydrophobic moiety may further extend beyond the lipid bilayer and be present externally. In these latter instances, it may be available for interaction with other moieties, including binding partners. Thus, depending on the embodiment, the hydrophobic moiety may (1) facilitate the synthesis and/or stabilize the coating of the nanoparticle, (2) add functionality to the nanoparticle by, for example, extending beyond the coating and being accessible to the external environment and potentially interacting with environmental factors, and/or (3) be attached to yet another moiety that is intended to reside externally to the nanoparticle and thereby optionally interact with the external environment and its factors. In this latter instance, the hydrophobic moiety serves as the bridge through the hydrophobic transmembrane region of, for example, a lipid bilayer coating. The additional moiety to which the hydrophobic moiety may be attached may be a reactive group that can be used to bind yet other factors (or moieties) to the nanoparticles. Thus, as an example, the hydrophobic moiety may be attached to a maleimide reactive group that ultimately is present at or beyond the external layer of the bilayer coating. The maleimide reactive group may be used to bind another moiety to the nanoparticle. In this way, a more universal or generic populations of nanoparticles may be synthesized and then later modified by binding of virtually any agent via the externally located reactive group. A variety of reactive groups are known in the art and the invention contemplates their use. Examples include without limitation amino groups such as primary and secondary amines, carboxyl groups, sulfhydryl groups, hydroxyl groups, aldehyde groups, azide groups, carbonyls, maleimide groups, haloacetyl (e.g., iodoacetyl) groups, imidoester groups, N-hydroxysuccinimide esters, and pyridyl disulfide groups.

The use of reactive groups attached to the oligonucleotide conjugate rather than attached to lipids that form the (e.g., bilayer) coat is significant, since it allows the precise placement and number of reactive groups per nanoparticle. Reactive groups attached to the lipids that form the lipid bilayer will not have a defined and static location since the lipids to which they are attached tend to be fluid in the bilayer.

In some embodiments, the hydrophobic moiety is attached to an agent such as a therapeutic agent, a prophylactic agent, an actively binding targeting agent and/or a diagnostic agent, as described in more detail below. In some embodiments, the hydrophobic moiety is itself an agent. In some embodiments, a hydrophobic moiety is not attached to an agent.

The number and location of the oligonucleotide conjugate, the hydrophobic moiety, and any additional moiety attached to the hydrophobic moiety relative to the nanoparticle may be random or it may be controlled, defined and known. Such control is achieved by the ability to precisely control the location at which the oligonucleotide conjugate hybridizes to the nanostructure core. Spatial control may be useful, for example, where the nanoparticles are intended to interact with each other and/or with another entity (such as an implant) in a particular spatial manner. The arrangement of the oligonucleotide conjugates may be periodic or non-periodic. It is to be understood that the number and location of hydrophobic moieties may be determined and varied during the process of designing and assembling/producing the nanostructure cores and the nanoparticles of the invention.

The oligonucleotide of the conjugate may be any sequence provided it interacts with the nanostructure. It need not possess any particular motifs such as immunostimulatory motifs. Accordingly, in some embodiments, the oligonucleotide is not immunostimulatory.

Nucleic Acids

The nucleic acid nanostructures, nucleic acid linkers, and oligonucleotide conjugates described herein may comprise naturally occurring and/or non-naturally occurring nucleic acids. If naturally occurring, the nucleic acids may be isolated from natural sources or they may be synthesized apart from their naturally occurring sources. Non-naturally occurring nucleic acids are synthetic.

The terms "nucleic acid," "oligonucleotide," and "oligodeoxyribonucleotide" are used interchangeably to mean multiple nucleotides. A nucleotide is a molecule comprising a sugar (e.g. a deoxyribose) linked to a phosphate group and to an exchangeable organic base, which is either a pyrimidine (e.g., cytosine (C), thymidine (T) or uracil (U)) or a purine (e.g., adenine (A) or guanine (G)). In some embodiments, the nucleic acid may be L-DNA. In some embodiments, the nucleic acid is not RNA or an oligoribonucleotide. Thus, in some embodiments, the nucleic acid nanostructure does not comprise RNA or oligoribonucleotides. In these embodiments, the nucleic acid nanostructure may be referred to as a DNA nanostructure. A DNA nanostructure however may still comprise base, sugar and backbone modifications.

Modifications

A nucleic acid nanostructure may be made of DNA, modified DNA, and combinations thereof. The oligodeoxyribonucleotides (also referred to herein as oligonucleotides) that are comprised by the nanostructure may have a homogeneous or heterogeneous (i.e., chimeric) backbone. The backbone may be a naturally occurring backbone such as a phosphodiester backbone or it may comprise backbone modification(s). In some instances, backbone modification results in a longer half-life for the oligonucleotides due to reduced nuclease-mediated degradation. This is turn results in a longer half-life and extended release profiles of the crosslinked complexes. Examples of suitable backbone modifications include but are not limited to phosphorothioate modifications, phosphorodithioate modifications, p-ethoxy modifications, methylphosphonate modifications, methylphosphorothioate modifications, alkyl- and arylphosphates (in which the charged phosphonate oxygen is replaced by an alkyl or aryl group), alkylphosphotriesters (in which the charged oxygen moiety is alkylated), peptide nucleic acid (PNA) backbone modifications, locked nucleic acid (LNA) backbone modifications, and the like. These modifications may be used in combination with each other and/or in combination with phosphodiester backbone linkages.

Alternatively or additionally, the oligonucleotides may comprise other modifications, including modifications at the base or the sugar moieties. Examples include nucleic acids having sugars which are covalently attached to low molecular weight organic groups other than a hydroxyl group at the 3' position and other than a phosphate group at the 5' position (e.g., a 2'-O-alkylated ribose), nucleic acids having sugars such as arabinose instead of ribose. Nucleic acids also embrace substituted purines and pyrimidines such as C-5 propyne modified bases (Wagner et al., *Nature Biotechnology* 14:840-844, 1996). Other purines and pyrimidines include but are not limited to 5-methylcytosine, 2-aminopurine, 2-amino-6-chloropurine, 2,6-diaminopurine, hypoxanthine. Other such modifications are well known to those of skill in the art.

Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863, and alkylphosphotriesters (in which the charged oxygen moiety is alkylated as described in U.S. Pat. No. 5,023,243 and European Patent No. 092574) can be prepared by automated solid phase synthesis using commercially available reagents. Methods for making other DNA backbone modifications and substitutions have been described (Uhlmann, E. and Peyman, A., Chem. Rev. 90:544, 1990; Goodchild, J., *Bioconjugate Chem.* 1:165, 1990).

Nucleic acids can be synthesized de novo using any of a number of procedures known in the art including, for example, the b-cyanoethyl phosphoramidite method (Beaucage and Caruthers *Tet. Let.* 22:1859, 1981), and the nucleoside H-phosphonate method (Garegg et al., *Tet. Let.* 27:4051-4054, 1986; Froehler et al., *Nucl. Acid. Res.* 14:5399-5407, 1986; Garegg et al., *Tet. Let.* 27:4055-4058, 1986, Gaffney et al., *Tet. Let.* 29:2619-2622, 1988). These chemistries can be performed by a variety of automated nucleic acid synthesizers available in the market. These nucleic acids are referred to as synthetic nucleic acids.

In some embodiments, oligonucleotides may be generated from larger nucleic acids such as but not limited to plasmids. Nucleic acids can be prepared from existing nucleic acid sequences (e.g., genomic or cDNA) using known techniques, such as those employing restriction enzymes, exonucleases or endonucleases. Nucleic acids prepared in this manner are referred to as isolated nucleic acid. An isolated nucleic acid generally refers to a nucleic acid that is separated from components with which it normally associates in nature. As an example, an isolated nucleic acid may be one that is separated from a cell, from a nucleus, from mitochondria, or from chromatin.

Lipids

In order to form certain nanoparticles of the invention, a nucleic acid nanostructure attached to a hydrophobic moiety through the use of a binding pair, as described herein or through the use of an oligonucleotide conjugate, is coated with lipids. The lipids may be isolated from a naturally occurring source or they may be synthesized apart from any naturally occurring source.

The lipids used herein may be amphipathic lipids having a hydrophilic and a hydrophobic portion. The hydrophobic portion typically orients into a hydrophobic phase, while the hydrophilic portion typically orients toward the aqueous phase. The hydrophilic portion may comprise polar or charged groups that include without limitation carbohydrates, phosphate, carboxylic, sulfato, amino, sulfhydryl, nitro, hydroxy and other like groups. The hydrophobic portion may comprise apolar groups that include without limitation long chain saturated and unsaturated aliphatic hydrocarbon groups and groups substituted by one or more aromatic, cyclo-aliphatic, or heterocyclic group(s). Examples of amphipathic compounds include, but are not limited to, phospholipids, aminolipids and sphingolipids.

In some embodiments, the lipids are phospholipids, though other lipid membrane components including but not limited to cholesterol, sphingomyelin, and cardiolipin may be additionally or alternatively used. Phospholipids or other lipids having the ability to form bilayers capable of coating nucleic acids may be used in the methods provided herein. Phospholipids include without limitation phosphatidylcholine, phosphatidylethanolamine, phosphatidylglycerol, phosphatidylinositol, phosphatidylserine, and the like.

The lipids used herein may be anionic or neutral (including zwitterionic and polar) lipids including anionic or neutral phospholipids. Neutral lipids exist in an uncharged or neutral zwitterionic form at a selected pH. At physiological pH, such lipids include, for example, dioleoylphosphatidylglycerol (DOPG), diacylphosphatidylcholine, diacylphosphatidylethanolamine, ceramide, sphingomyelin, cephalin, cholesterol, cerebrosides and diacylglycerols. Examples of zwitterionic lipids include without limitation dioleoylphosphatidylcholine (DOPC), dimyristoylphosphatidylcholine (DMPC), and dioleoylphosphatidylserine (DOSE). An anionic lipid is a lipid that is negatively charged at physiological pH. Anionic lipids include without limitation phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

Collectively, anionic and neutral lipids are referred to herein as non-cationic lipids in order to exclude cationic lipids from the class. Such lipids may contain phosphorus but they are not so limited. Examples of non-cationic lipids used herein include without limitation lecithin, lysolecithin, phosphatidylethanolamine, lysophosphatidylethanolamine, dioleoylphosphatidylethanolamine (DOPE), dipalmitoyl phosphatidyl ethanolamine (DPPE), dimyristoylphosphoethanolamine (DMPE), distearoyl-phosphatidyl-ethanolamine (DSPE), palm itoyloleoyl-phosphatidylethanolamine (POPE) palm itoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), palmitoyloleyolphosphatidylglycerol (POPG), 16-O-monomethyl PE, 16-O-dimethyl PE, 18-1-trans PE, palmitoyloleoyl-phosphatidylethanolamine (POPE), 1-stearoyl-2-oleoyl-phosphatidyethanolamine (SOPE), phosphatidylserine, phosphatidylinositol, sphingomyelin, cephalin, cardiolipin, phosphatidic acid, cerebrosides, dicetylphosphate, and cholesterol.

Additional nonphosphorous containing lipids used herein include stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide and the like, diacylphosphatidylcholine, diacylphosphatidylethanolamine, ceramide, sphingomyelin, cephalin, and cerebrosides. Lipids such as lysophosphatidylcholine and lysophosphatidylethanolamine may be used in some instances.

Non-cationic lipids for use herein also include polyethylene glycol-based polymers such as PEG 2000, PEG 5000 and polyethylene glycol conjugated to phospholipids or to ceramides (referred to as PEG-Cer).

The nanoparticles may or may not comprise cationic lipids. Examples of cationic lipids include 1,2-dioleoyl-3-trimethylammonium-propane (DOTAP), 1,2-dioleoyl-3-dimethylammonium-propane (DODAP), Dimethyldioctadecylammonium (DDAB), 1,2-di-O-octadecenyl-3-trimethylammonium propane (DOTMA), 1,2-dilauroyl-sn-glycero-3-ethylphosphocholine (Ethyl PC), and 3β-[N—(N', N'-dimethylaminoethane)-carbamoyl]cholesterol hydrochloride (DC-Cholesterol-HCl).

In some instances, modified forms of lipids may be used including without limitation forms modified with detectable labels such as fluorophores and/or reactive groups such as maleimide (e.g., dioleoyl-phosphatidylethanolamine 4-(N-maleimidomethyl)-cyclohexane-1-carboxylate (DOPE-mal) and 1,2-dipalmitoyl-sn-glycero-3-phosphoethanolamine-N-[4-(p-maleimidophenyl)-butyramide] (MBP)), among others. In some instances, the lipid is a lipid analog that emits signal (e.g., a fluorescent signal). Examples include without limitation 1,1'-dioctadecyl-3,3,3',3'-tetramethylindotricarbocyanine iodide (DiR) and 1,1'-dioctadecyl-3,3,3',3'-tetramethylindodicarbocyanine (DiD). The use of detectably labeled lipids facilitates monitoring and assessment of the nanoparticle, including assessment of where the nanoparticle travels and resides in vivo, its stability, its half-life, and the like.

It is to be understood that the invention does not rely on electrostatic interactions between the coat components and the nucleic acids of the nanostructure core in order to form and stabilize the nanoparticle. Thus, while the nucleic acids of the nanostructure are typically negatively charged, the lipid coat need not have an overall positive charge in order for the nanoparticles to form. In some instances, the overall charge of the lipid coating is neutral or anionic. Such a coating may still comprise cationic lipids but they may be at a sufficiently low abundance that the overall charge of the nanoparticle is neutral or negative. In some instances, the overall charge of the lipid coating is positive (or cationic).

The invention contemplates the use of single lipids (referred to herein as homogeneous lipids) or combinations of lipids (referred to herein as heterogeneous lipids). If combinations are used, they may be combinations of anionic lipids, combinations of neutral lipids, or combinations of anionic and neutral lipids. Such combinations may be made from a range of molar ratios. For example, neutral lipids and anionic lipids may be used in molar ratios that range from 1:100 to 100:1, or in a range from 1:10 to 10:1 or in range from 1:1 to 10:1.

The lipids may or may not be conjugated to polyethylene glycol (PEG).

Methods of Producing Nanoparticles

The invention further provides methods for producing the nanoparticles of the invention. Generally, the nanoparticles are produced by (a) combining a nucleic acid nanostructure with a hydrophobic moiety through the use of a binding pair (e.g., biotin/streptavidin) or through the use of an oligonucleotide conjugate that comprises a hydrophobic moiety, to produce a hydrophobic moiety-linked nanostructure, and (b) combining the hydrophobic moiety-linked nanostructure with lipids and a surfactant. The lipids form a coat (or coating, as the terms are used interchangeably herein) over the nanostructure. It has been observed in accordance with the invention that the coating tends to "shrink-wrap" around the nanostructure core, almost akin to a "skin" on the core. In this way, the resultant nanoparticle shape corresponds to (i.e., generally mimics) the nanostructure core shape. Accordingly, the invention provides nanoparticles of defined, predetermined shape that are protected from factors that tend to destabilize and/or degrade nucleic acids.

Examples of surfactants that can be used herein include polysorbates (Tween™), sodium dodecyl sulfate (sodium lauryl sulfate), lauryl dimethyl amine oxide, cetyltrimethyl-ammonium bromide (CTAB), polyethoxylated alcohols, polyoxyethylene sorbitan, octoxynol (Triton X100™), N,N-dimethyldodecylamine-N-oxide, hexadecyltrimethylammonium bromide (HTAB), polyoxyl 10 lauryl ether, Brij 721™, bile salts (sodium deoxycholate, sodium cholate), polyoxyl castor oil (Cremophor™), nonylphenol ethoxylate (Tergitol™), cyclodextrins, lecithin, and methylbenzethonium chloride (Hyamine™).

The nanoparticles are typically isolated and/or purified. Isolation, as used herein, refers to the physical separation of the desired entity (e.g., nanoparticles, nanostructures, etc.) from the environment in which it normally or naturally exists or the environment in which it was generated. The isolation may be partial or complete. Complete isolation typically refers to a purified product. The degree of isolation (and thus the degree of purification) may be characterized in terms of the nature and amount of contaminants still present in a composition that comprises the product of interest. Isolation and/or purification may be accomplished by manual or automatic means and may be performed using one or more steps in the synthesis process.

As an example, isolation of the nanostructure may be carried out by running a hybridization reaction mixture on a gel and isolating nucleic acid species that migrate at a particular molecular weight that can be distinguished from the nucleic acid substrate species and the spurious products of the hybridization reaction. As another example, isolation of nanoparticles may be carried out using a buoyant density gradient, sedimentation gradient centrifugation, or through filtration means. Isolated nanoparticles of the invention include those that are physically separated (in whole or in part) from empty liposome-like particles or free nucleic acid nanostructures.

As discussed below in greater detail, the nanoparticle may be produced with a nucleic acid nanostructure directly or indirectly linked to an oligonucleotide conjugate having a hydrophobic moiety. In embodiments where single-stranded nucleic acid handles are used as intermediary molecules, the oligonucleotide conjugate and handles may be combined at a molar ratio of, for example, 1-5 conjugates to 1 handle including 1 conjugate to 1 handle and 5 conjugates to 1 handle. Accordingly, there would be 1-5 (or more) hydrophobic moieties per handle.

In some embodiments, the nucleic acid nanostructures, hydrophobic conjugates and surfactant are combined, and then lipids (whether homogenous or heterogeneous) are added. The surfactant is removed by dialysis, thereby producing coated nanoparticles. The mixture is expected to contain lipid-coated nanoparticles in the shape of their nucleic acid nanostructure core, empty liposome-like particles, and free nucleic acid nanostructures. The mole ratio of lipid to nucleic acid may be in the range of 200:1 to 5:1, 100:1 to 5:1, 100:1 to 10:1, or 50:1 to 10:1, although it is not limited.

The production process also typically includes steps to remove unreacted substrates and unwanted byproducts of the reaction. Uncoated nucleic acid nanostructures may be removed by any means including chemical means (e.g., acid hydrolysis), enzymatic means (e.g., nuclease digestion such as but not limited to exonuclease digestion), and/or mechanical means (e.g., centrifugation). Empty liposome-particles may be removed by certain chemical means and/or mechanical means (e.g., centrifugation, buoyant density separation, etc.).

The nanoparticles may be further modified or manipulated post-synthesis for example by addition of an agent. The nanoparticles may contain agents intended for use in vivo or in vitro including without limitation therapeutic agents, prophylactic agents, and diagnostic agents (e.g., detectable labels). For example, a nanoparticle of the invention may be loaded with an agent. The agent may be specifically attached to the oligonucleotide conjugate (and optionally presented to the external environment) or it may be present in the nanostructure (optionally, non-specifically). In some embodiments, an agent may be covalently linked to the hydrophobic moiety of the oligonucleotide conjugate and may be present on the surface of the nanoparticle. In some embodiments, an agent may be present within the nanoparticle, including within the nanostructure. In some embodiments, agents may be present at the surface and internally, and such agents may be the same or they may be different. The relative ratios of such agents may vary.

The methods are not intended to be limited in these regards as the steps may be carried out in any manner that is convenient and suitable.

Agents

As discussed above, a nanoparticle may contain an agent that is intended for use in vivo and/or in vitro. As used herein, an agent is any atom, molecule, or compound that can be used to provide benefit to a subject (including without limitation prophylactic or therapeutic benefit) or that can be used for diagnosis and/or detection (for example, imaging) in vivo, or that may be used for effect in an in vitro setting (for example, a tissue or organ culture, a clean-up process, and the like). The agents may be without limitation therapeutic agents and diagnostic agents. Examples of agents for use with any one of the embodiments described herein are described below.

The agent may be covalently or non-covalently attached to the nano-particle including for example the hydrophobic moiety. The location and nature of the linkage between the agent and the nanoparticle will depend upon the function of the agent. As an example, the agent may be intended to release (including slow release) from the nanoparticle, and in that case the linkage between the agent and the nanoparticle will be chosen to achieve the desired release profile. Covalent attachment of agents to a hydrophobic moiety may involve the use of bonds that can be cleaved under physiological conditions or that can be caused to cleave specifically upon application of a stimulus such as light, whereby the agent can be released. Readily cleavable bonds include readily hydrolyzable bonds, for example, ester bonds, amide bonds and Schiff's base-type bonds. Bonds that are cleavable by light are known. In certain instances, the agent may be inactive in its bound form and activated only when released.

In some instances, the agent may be combined with the hydrophobic moiety prior to contact with the lipids, or an agent may be combined with a pre-formed nanoparticle.

The invention contemplates in some aspects the delivery of nanoparticles or nanoparticles loaded with an agent either systemically or to localized regions, tissues, or cells. Any agent may be delivered using the methods of the invention provided that it can be loaded onto or into the nanoparticle. Because such processes are relatively innocuous, it is expected that virtually any agent may be used.

A nanoparticle may be synthesized and stored in, for example, a lyophilized and optionally frozen form. The agent should be stable during such storage procedures and times.

The agent may be naturally occurring or non-naturally occurring. Naturally occurring agents include those capable of being synthesized by the subjects to whom the nanoparticles are administered. Non-naturally occurring are those that do not exist in nature normally, whether produced by plant, animal, microbe or other living organism.

The agent may be without limitation a chemical compound including a small molecule, a protein, a polypeptide, a peptide, a nucleic acid, a virus-like particle, a steroid, a proteoglycan, a lipid, a carbohydrate, and analogs, derivatives, mixtures, fusions, combinations or conjugates thereof. The agent may be a prodrug that is metabolized and thus converted in vivo to its active (and/or stable) form. The invention further contemplates the loading of more than one type of agent in a nanoparticle and/or the combined use of nanoparticles comprising different agents.

One class of agent is peptide-based agents such as (single or multi-chain) proteins and peptides. Examples of peptide-based agents for use with any of the aspect and embodiments described herein include without limitation antibodies, single chain antibodies, antibody fragments, enzymes, co-factors, receptors, ligands, transcription factors and other regulatory factors, some antigens (as discussed below), cytokines, chemokines, hormones, and the like.

Another class of agents that can be delivered using the nanoparticles of the invention includes chemical compounds that are non-naturally occurring.

A variety of agents that are currently used for therapeutic or diagnostic purposes can be delivered according to the invention and these include without limitation imaging agents, immunomodulatory agents such as immunostimulatory agents and immunoinhibitory agents (e.g., cyclosporine), antigens, adjuvants, cytokines, chemokines, anti-cancer agents, anti-infective agents, nucleic acids, antibodies or fragments thereof, fusion proteins such as cytokine-antibody fusion proteins, Fc-fusion proteins, analgesics, opioids, enzyme inhibitors, neurotoxins, hypnotics, anti-histamines, lubricants, tranquilizers, anti-convulsants, muscle relaxants, anti-Parkinson agents, anti-spasmodics, muscle contractants including channel blockers, miotics and anti-cholinergics, anti-glaucoma compounds, modulators of cell-extracellular matrix interactions including cell growth inhibitors and anti-adhesion molecules, vasodilating agents, inhibitors of DNA, RNA or protein synthesis, anti-hypertensives, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, targeting agents, neurotransmitters, proteins, cell response modifiers, and vaccines.

In some embodiments, an agent is a diagnostic agent such as an imaging agent. As used herein, an imaging agent is an agent that emits signal directly or indirectly thereby allowing its detection in vivo. Imaging agents such as contrast agents and radioactive agents can be detected using medical imaging techniques such as nuclear medicine scans and magnetic resonance imaging (MRI). Imaging agents for magnetic resonance imaging (MRI) include Gd(DOTA), iron oxide or gold nanoparticles; imaging agents for nuclear medicine include $^{201}$Tl, gamma-emitting radionuclide 99 mTc; imaging agents for positron-emission tomography (PET) include positron-emitting isotopes, (18)F-fluorodeoxyglucose ((18)FDG), (18)F-fluoride, copper-64, gadoamide, and radioisotopes of Pb(II) such as 203Pb, and 11In; imaging agents for in vivo fluorescence imaging such as fluorescent dyes or dye-conjugated nanoparticles. In some embodiments, the agent to be delivered is conjugated, or fused to, or mixed or combined with an imaging agent.

Subjects

When the shaped nanoparticles are used in vivo, the invention can be practiced in virtually any subject type that is likely to benefit prophylactically, therapeutically, or prognostically from the delivery of nanoparticles of the invention as contemplated herein.

Human subjects are preferred subjects in some embodiments of the invention. Subjects also include animals such as household pets (e.g., dogs, cats, rabbits, ferrets), livestock or farm animals (e.g., cows, pigs, sheep, chickens, and other poultry), horses such as thoroughbred horses, laboratory animals (e.g., mice, rats, rabbits), and the like. Subjects also include fish and other aquatic species.

The subjects to whom the nanoparticles are delivered may be normal subjects. Alternatively, they may have or may be at risk of developing condition that can be diagnosed or that can benefit or that can be prevented from systemic or localized delivery of one or more particular agents. Such conditions include cancer (e.g., solid tumor cancers), infections (particularly infections localized to particular regions or tissues in the body), autoimmune disorders, allergies or allergic conditions, asthma, transplant rejection, diabetes, heart disease, and the like.

In some instances, the agents are delivered to prevent the onset of a condition whether or not such condition is considered a disorder.

In some instances, the subject may be in need of an implant or may have already received an implant and the nanoparticles of the invention are to be used in conjunction with such implant therapy.

Amounts, Administration, Formulations

When agents are administered to a subject, they are administered in effective amounts. An effective amount is a dosage of the agent sufficient to provide a medically desirable result. The effective amount will vary with the particular condition being treated, the age and physical condition of the subject being treated, the severity of the condition, the duration of the treatment, the nature of the concurrent or combination therapy (if any), the specific route of administration and like factors within the knowledge and expertise of the health practitioner. It is preferred generally that a maximum dose be used, that is, the highest safe dose according to sound medical judgment.

Administration of a nanoparticle, with or without an agent, may be by a systemic route such as intravenous, intramuscular, intradermal, intraperitoneal, subcutaneous, by inhalation, or other parenteral routes. Administration may be oral or it may be through a localized route such as injection or topical administration to a tissue (e.g., skin, mucosa such as oral, vaginal, rectal, gut, or lung mucosa), an organ, a tumor, a lesion, a site of infection such as an abscess, and the like. The route of administration in some instances will be governed by the particular application.

The invention provides pharmaceutical compositions. Pharmaceutical compositions are sterile compositions that comprise nanoparticles and, in some embodiments, agent(s), preferably in a pharmaceutically-acceptable carrier. The term "pharmaceutically-acceptable carrier" means one or more compatible solid or liquid filler, diluents or encapsulating substances which are suitable for administration to a human or other subject contemplated by the invention. The term "carrier" denotes an organic or inorganic ingredient, natural or synthetic, with which the cells, nanoparticles and agent(s) are combined to facilitate administration. The components of the pharmaceutical compositions are commingled in a manner which precludes interactions that would substantially impair their desired pharmaceutical efficiency.

A nanoparticle, when delivered systemically, may be formulated for parenteral administration by injection, e.g., by bolus injection or continuous infusion. Formulations for injection may be presented in unit dosage form, e.g., in ampoules or in multi-dose containers. Pharmaceutical parenteral formulations include aqueous solutions of the ingredients. Aqueous injection suspensions may contain substances that increase the viscosity of the suspension, such as sodium carboxymethyl cellulose, sorbitol, or dextran. Alternatively, suspensions of ingredients may be prepared as oil-based suspensions. Suitable lipophilic solvents or vehicles include fatty oils such as sesame oil, or synthetic fatty acid esters, such as ethyl oleate or triglycerides.

The following Examples are included for purposes of illustration and are not intended to limit the scope of the invention.

EXAMPLES

Materials

Sources of DNA included viral phage single-stranded DNA obtained from purification of phage genome using standard methods (Douglas, S. M. (2009)) and DNA oligonucleotides synthesized by Bioneer Inc, measuring between 18 and 100 nucleotides in length. 1,2-Dioleoyl-sn-glycero-3-phosphocholine (DOPC), 1,2,-dioleoyl-sn-glycero-3-phospho-L-serine (DOPS), 1,2-dioleoyl-sn-glycero-3-phosphoethanolamine-N-[methoxy(polyethylene glycol)-2000] (PEG2000-PE), and 1,2-dipalmitoyl-sn-glycero-3-phosphoethanolamine-N-(lissamine rhodamine B sulfonyl) (Rhod-PE), and 1,2-dioleoyl-sn-glycero-3-phosphoethanolamine-N-[4-(p-maleimidophenyl)butyramide] (DOPE-maleimide) were purchased from Avanti Polar Lipids. The mini-extruder apparatus and polycarbonate extrusion filters were purchased from Avanti Polar Lipids. Amicon Ultra-4 Centrifugal Filter Units were purchased from Millipore. Illustra Microspin G-25 desalting columns were purchased from GE Healthcare. Optiprep Density Gradient medium was purchased from Sigma-Aldrich. All other chemicals and disposables were obtained from Sigma-Aldrich.

Methods

Lipid Preparation

1. Volumes of the lipid products in chloroform from Avanti were mixed to produce a solution containing $4.5 \times 10^{-6}$ mols of lipid with the following molar contributions: DOPC=79.2%, DOPS=15.0%, PEG2000-PE=5%, Rhod-PE=0.8%.
2. The chloroform was evaporated under a nitrogen gas stream.
3. The lipid film was placed under vacuum overnight.
4. 300 µL of encapsulation buffer (5 mM Tris, 1 mM EDTA, 10 mM NaCl, 10 mM $MgCl_2$, pH 7.5) was added to the lipid film. This was shaken vigorously for one hour to produce a solution of dispersed lipid structures.
5. The solution of lipids was freeze-dried by placing on liquid nitrogen for approximately 15 seconds, then transferring the tube to a room-temperature water bath for approximately 15 seconds until thawed. This was repeated a total of 7 times.
6. The solution of lipids was then extruded through a mini-extruder apparatus, using a polycarbonate membrane with 0.2 micron (µ) pore size. The sample was passed through the filter a total of 21 times.
7. The lipids were then either used immediately for coating of nucleic acid nanostructures, or were stored at 4° C., light-protected until use.

DNA Nanostructure Preparation

1. DNA nanostructures were designed and prepared according to previously published methods (Douglas, S. M. et al. (2009); Douglas, S. M. et al. *Nucleic Acids Research* 37, 5001 (2009); Dietz, H. et al. *Science* 325, 725-730 (2009); Ke, Y. et al. *J. Am. Chem. Soc.* 131, 15903-15908 (2009); Liedl, T. et al. *Nature Nanotech* 5, 520-524 (2010).
2. Structures were designed to present between 5 and 100 single-stranded DNA handles outwards from the structure for annealing to hydrophobic moieties, and between 2 and 20 single-stranded handles of an alternate sequence facing inward for attachment of contrast agents.
3. In brief, an 800 µL solution composed of 50 nM single-stranded DNA phage "scaffold" strand, 250 nM of each oligonucleotide "staple" strand, a concentration of $MgCl_2$ between 10-22 mM that was determined independently for each nanostructure design, and buffer (5 mM Tris, 1 mM EDTA, 10 mM NaCl, pH 7.5) was mixed and placed on a Peltier thermal block for a "folding" program that was determined appropriate for each structure.
4. After completion of the folding program, the monomer DNA nanostructures were purified away from dimers, multimers and excess nucleotides using sedimentation ultracentrifugation through a glycerol gradient previously optimized as appropriate for the task.
5. After isolating the monomer DNA nanostructures via the glycerol gradient, glycerol was removed by buffer exchange using an Amicon Ultra-4 Centrifugal Filter Unit, with a total of 3 washes.
6. The concentration of the DNA nanostructures was characterized by absorption of light at 260 nm, and using Beer's Law.

Synthesis of Oligonucleotide-Hydrophobic Moiety Conjugates

Conjugates of oligonucleotides and lipids or peptides were produced as previously described using PE-maleimide (Yoshina-Ishii, C. et al. *J. Am. Chem. Soc.* 127, 1356-1357 (2005), incorporated herein by reference).

In brief, oligonucleotides or peptides with monothiol or cysteine functional groups were reduced by addition of TCEP at a 1000-times molar ratio to target.

1. The reduced product was passed through an Illustra G-25 desalting column and was immediately added to PE-maleimide in a 1:1 ratio.
2. The produce was purified by high-performance liquid chromatography.
3. The product was characterized by UV-VIS absorption at 260/280 nm.

DNA Nanostructure Annealing Oligonucleotide-Hydrophobic Moiety Conjugates

1. Volumes of purified nanostructures at 20 µg/mL were mixed with surfactant (e.g., octyl glucoside, OG) at 1.5× its critical micelle concentration (e.g., 1% for OG), the oligonucleotide-hydrophobic guest molecules (DNA-lipid or DNA-peptide) and with oligonucleotide-contrast agent (DNA-fluorophore or DNA-gold nanoparticle) at a molar ratio of 5 conjugates per single-stranded handle.
2. These were incubated for a minimum of 10 minutes (2 hours typically, no max) at a temperature between 5 and 50° C. to allow annealing between complimentary DNA-conjugates and the single-stranded handles.
3. A 2× volume of the functionalized DNA nanostructure was then mixed with 1× volume of the liposome preparation, e.g., 40 µL and 20 µL. This was incubated at room temperature with no shaking or moderate shaking for a minimum of several minutes (1 hour typically, no max).
4. An equal volume (e.g., 60 µL) of buffer (5 mM Tris, 1 mM EDTA, 10 mM NaCl, 10 mM $MgCl_2$) was added to the sample.
5. The sample was then transferred to a dialysis cassette having a molecular weight cut-off of at least 7,000 Daltons but no more than 30,000 Daltons, and was incubated for a minimum of 24 hours and a maximum of 72 hours in buffer with routine changes to remove the surfactant.
6. The sample was retrieved from the dialysis cassette.

Purification of Lipid-Coated Nanoparticles
1. Structures were purified using equilibrium ultracentrifugation and Optiprep Density Gradient medium. Step-wise gradients were prepared based on densities determined as appropriate for a particular nanostructure.
2. Ultracentrifugation was performed for 15 minutes to 3 hours at 100,000 to 400,000×g.
3. Fractions from the resulting gradient were collected using standard methods.
4. Fractions were analyzed for the presence of lipid-coated DNA nanostructures by measuring fluorescence in a 96-well fluorescence plate, and imaging using a Typhoon imaging station.
5. Fractions containing lipid-coated DNA nanostructures were purified and buffer-exchanged using a desalting column.
6. Structures were characterized by transmission electron microscopy and negative staining using uranyl formate.

Example 1

Encapsulation of DNA Nanostructures

Figure 8:
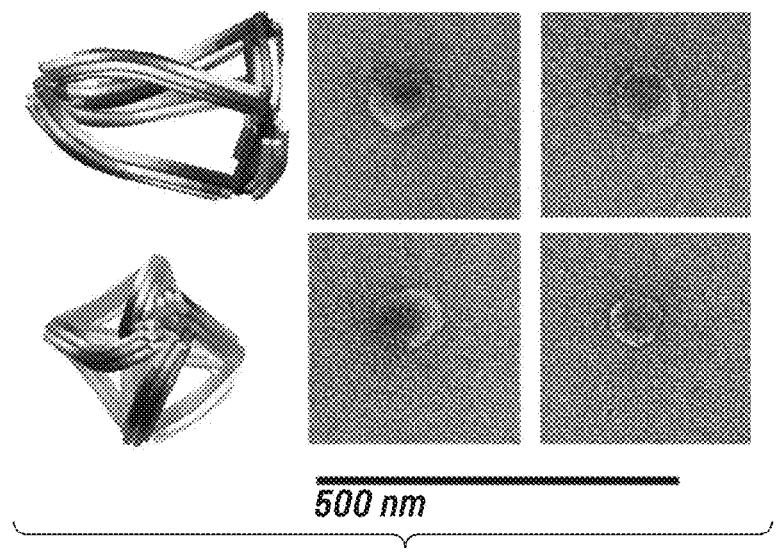
FIG. 8: Examples of coated DNA nanostructures. (Left) Schematic showing an irregular/abstract (e.g., "torpedo") DNA nanostructure. (Right) Transmission electron microscopy (TEM) images of examples of irregular/abstract DNA nanostructures after lipid coating.
Figure 9:
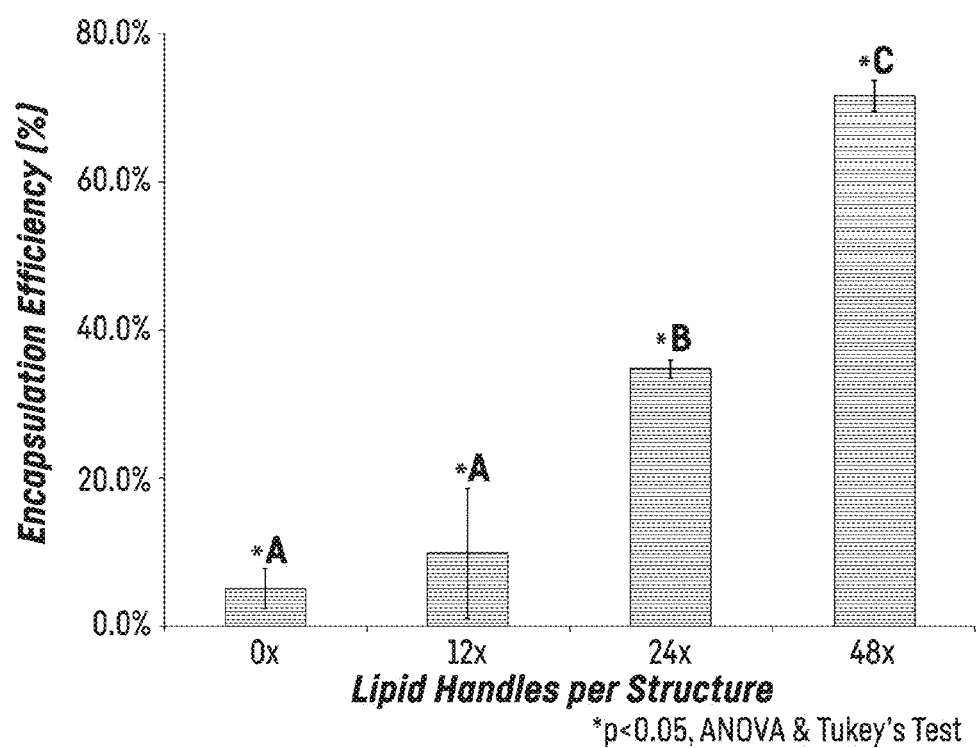
FIG. 9: Dependence of coating efficiency on the number of oligonucleotide conjugates. Coating of the DNA nanostructures by lipid bilayers is dependent on the number of oligonucleotide conjugates attached to the nanostructures. The graph shows the coating efficiency, as measured by a staining assay, and its dependence on the number of oligonucleotide conjugates attached to the DNA nanostructure.
Figure 10A:
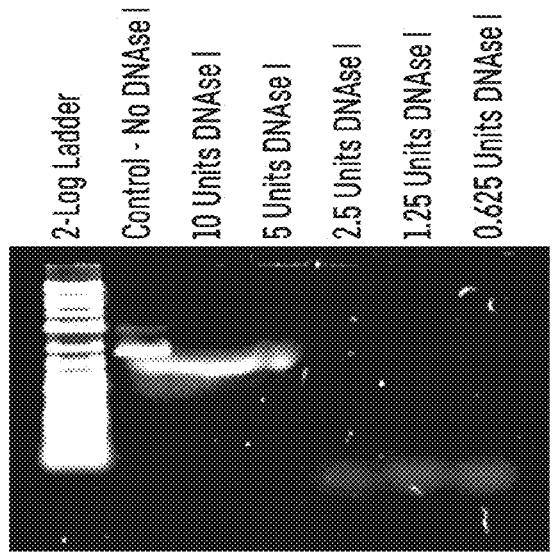
FIGS. 10A and 10B: DNase I nuclease protection by coating. The left image shows a gel where DNase I nuclease was titrated against naked DNA nanostructures. Even low amounts of nuclease caused complete degradation of the nanostructures. The coated DNA nanostructures of the invention provided protection against DNase activity, as shown on the right. DNA nanostructures coated using 48 oligonucleotide conjugates on the nanostructure were present after exposure to DNase I nuclease, as measured by a DNA staining protocol. By comparison, DNA nanostructures that were not coated (zero oligonucleotide conjugates) were almost completely digested by DNase I nuclease.
Figure 10B:
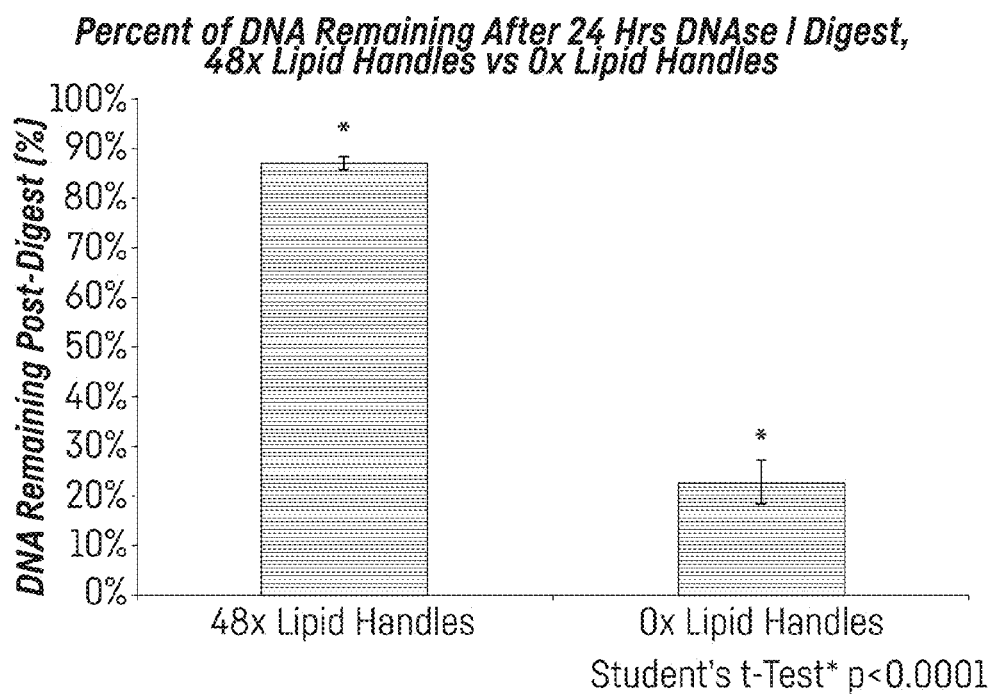

The irregular-shaped "torpedo" DNA nanostructure shown in FIG. 8 was synthesized using the methods provided herein. Specifically, an M13 single-stranded DNA scaffold (length 7308 nucleotides) was folded with a set of 186 synthetic oligonucleotides (ONTs). A pool of the ONTs was mixed with scaffold at a ratio of 5 of each ONT per scaffold in Tris-EDTA buffer with 12 mM $MgCl_2$. The mixture was heated to 85° C., then cooled to 25° C. for 15 hours. The monomeric DNA nanostructures were purified from excess staples/oligonucleotides and mis-folded particles using glycerol gradient centrifugation. Oligonucleotide conjugates (e.g., hydrophobic moieties attached to single-stranded oligonucleotides) were then added to the DNA nanostructures in the presence of 2% octylglucoside surfactant. The oligonucleotide sequence was complimentary to 40 single-stranded regions present on the outside of the nanostructure, and annealing was carried out for 2 hours at 35° C. The annealed structure was again purified away from excess conjugate by glycerol gradient centrifugation. 40 µL of the purified product was then mixed with 20 µL of 200 nm liposomes containing DOPC, DOPS, PEG-PE and rhodamine-PI. This mixture was incubated for 1 hour at room temperature. 60 µL of Tris-EDTA buffer and 10 mM $MgCl_2$ was added to the solution, and the entire volume was then transferred into a dialysis cassette (7000 molecular weight cut-off) and floated in 2 L of buffer for 48 hours. The sample was then recovered from the dialysis cassette. Imaging was carried out by transmission electron microscopy (TEM) on carbon-formvar grids, using uranyl formate as a negative stain.

Example 2. Coating Efficiency is a Function of Oligonucleotide Conjugate Number

DNA nanostructures (curved octahedron folded from M13 single-stranded genome of length 7308 nucleotides) were synthesized as described in Example 1. The nanostructures were designed and synthesized to present a variable number (0-48) of single-stranded oligonucleotide "handles" on their outer surface, all of the same sequence. A oligonucleotide conjugate was annealed to the structures using the method described in Example 1, at a conjugate:handle molar ratio of 10:1. The annealed structures were purified by glycerol gradient centrifugation. Nanostructure coating was conducted as described in Example 1. Following completion of the coating process, the coating efficiency of the samples was determined by a PicoGreen® exclusion assay. PicoGreen® is a highly sensitive stain specific for double-stranded DNA. Samples were diluted 1:5 with buffer, 90 µL total. Additionally, a standard curve of stock DNA nanostructure was produced from 4 µg/mL and with 7× 1:2 dilutions in buffer. A solution of PicoGreen® reagent in Tris-EDTA buffer with 10 mM $MgCl_2$ was prepared, with a total volume that would provide 20 µL per sample/standard× n=3 replicates. A second solution was prepared, the same as the first, except with the inclusion of 2% octylglucoside surfactant. 17.5 µL of both buffers was dispensed into 3× wells of a 384-well fluorescence plate for each sample and each standard to be measured. 2.5 µL of each sample or standard was then added to 3× wells of each buffer. The plate was incubated for 5 minutes in the dark, and fluorescence was read on a plate reader at the appropriate wavelength for the PicoGreen® stain.

Standard curve functions were determined for both the octylglucoside-positive and octylglucoside-negative buffers. The concentration of nanostructures was then determined for both buffers. The concentration in surfactant-negative buffer is a measure of only the nanostructures that are not coated (External Fraction), as the PicoGreen® reagent is unable to penetrate through the lipid bilayer to stain coated nanostructures. The concentration in surfactant-positive buffer is a measure of the total nanostructures present in the sample, as the surfactant destabilizes the membrane and allows staining of the entire volume of the nanostructure. Coating efficiency was then calculated as (Total Sample Concentration−External Fraction Concentration)/(Total Sample Concentration).

Example 3. Protection from DNase Nuclease Digestion

To determine the sensitivity of DNA nanostructures to nuclease activity of DNase nuclease I, variable amounts (0.625-10.0 units) of DNase I were added to 20 µL of DNA nanostructures at a concentration of 20 µg/mL, 25 µL total.

The samples were incubated for 30 minutes at 37° C., and were then immediately added into the wells of a 1.5% agarose gel containing SYBR® Safe nucleic acid stain and 10 mM $MgCl_2$. The samples were separated by electrophoresis for 3 hours at 60 volts, and the gel was imaged for fluorescence. To determine whether coated DNA nanostructures were protected from DNA I nuclease activity, coated DNA nanostructures were prepared as described in Example 2 (48 oligonucleotide conjugates, n=3). After completion of the coating, 25 µL of the encapsulated samples were transferred into new microcentrifuge tubes, and 10 units of DNase I nuclease were added, or an equivalent volume of buffer as negative controls. The samples were incubated overnight at 37° C. The following day, the concentration of DNA nanostructures was determined for the DNase I-positive and the DNase I-negative samples as described in Example 2. The percent of DNA remaining post-digestion was then calculated as a ratio of (DNA concentration in nuclease-positive sample)/(DNA concentration in nuclease-negative sample).

EQUIVALENTS AND SCOPE

Those skilled in the art will recognize or be able to ascertain using no more than routine experimentation many equivalents to the specific embodiments described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviations, per the practice in the art. Alternatively, "about" can mean a range of up to 20%, up to 10%, up to 5%, or up to 1% of a given value. Alternatively, the term can mean within an order of magnitude, for example, within 5-fold, or within 2-fold, of a value. Where particular values are described in the application and claims, unless otherwise stated the term "about" meaning within an acceptable error range for the particular value should be assumed.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the methods of the invention can be excluded from any one or more claims, for any reason, whether or not related to the existence of prior art.

Each of the foregoing patents, patent applications and references is hereby incorporated by reference, particularly for the teaching referenced herein.

What is claimed is:

1. A nanoparticle comprising a nucleic acid nanostructure core and a lipid coating, wherein the nucleic acid nanostructure has a void volume of at least 25% and is attached to a hydrophobic moiety through
   (a) a single-stranded oligonucleotide conjugate comprising the hydrophobic moiety, or
   (b) a binding pair, one member of which is attached to the nanostructure and one member of which is attached to the hydrophobic moiety,
   wherein the hydrophobic moiety is in contact with the lipid coating.

2. The nanoparticle of claim 1, wherein the lipid coating is a lipid bilayer having an interior layer, a transmembrane region, and an exterior layer.

3. The nanoparticle of claim 2, wherein the hydrophobic moiety is positioned within the transmembrane region of the lipid bilayer, or extends through the lipid bilayer and is positioned exterior to the nanoparticle.

4. The nanoparticle of claim 1, wherein the hydrophobic moiety is a lipid, a peptide, or a surfactant.

5. The nanoparticle of claim 1, wherein the oligonucleotide conjugate is hybridized to the nucleic acid nanostructure, or is hybridized to a single-stranded nucleic acid handle that is attached to the nucleic acid nanostructure.

6. The nanoparticle of claim 5, wherein the single-stranded nucleic acid handle is covalently attached to the nucleic acid nanostructure.

7. The nanoparticle of claim 1, wherein the binding pair is an avidin-biotin binding pair, an antigen-antibody binding pair or a receptor-ligand binding pair.

8. The nanoparticle of claim 7, wherein the binding pair is biotin and streptavidin.

9. The nanoparticle of claim 1, wherein the lipid coating is heterogeneous.

10. The nanoparticle of claim 1, wherein the lipid coating comprises a phospholipid, an aminolipid, a sphingolipid, or a combination thereof.

11. The nanoparticle of claim 1, wherein the lipid coating comprises cholesterol, sphingomyelin, cardiolipin, or a combination thereof.

12. The nanoparticle of claim 1, wherein the lipid coating comprises a neutral lipid or a cationic lipid.

13. The nanoparticle of claim 12, wherein the lipid coating comprises a neutral lipid that is uncharged or is zwitterionic.

14. The nanoparticle of claim 1, wherein the lipid coating has an overall neutral or positive charge.

15. The nanoparticle of claim 1, wherein the shape of the lipid coating is substantially the same as the shape of the nucleic acid nanostructure.

16. The nanoparticle of claim 1, wherein the defined shape is selected from the group consisting of: a hemi-sphere, a cube, a cuboidal, a tetrahedron, a cylinder, a cone, an octahedron, a prism, a sphere, a pyramid, a dodecahedron, a tube, and an irregular shape.

17. The nanoparticle of claim 1, wherein the nanoparticle may have a cross section length of less than 1000 nanometers.

18. The nanoparticle of claim 1, further comprising an agent, optionally attached to the nanostructure core, or encapsulated within a volume created by the lipid coating.

19. The nanoparticle of claim 18, wherein an agent is attached to the hydrophobic moiety.

20. The nanoparticle of claim 18, wherein the agent is a therapeutic agent, a prophylactic agent, or a diagnostic agent.

21. The nanoparticle of claim 1, wherein the nanoparticle does not comprise an agent.

22. A composition comprising the nanoparticle of claim 1 and a carrier or excipient.

23. The nanoparticle of claim 1, wherein the nucleic acid nanostructure is three-dimensional.

24. The nanoparticle of claim 1, wherein the nucleic acid nanostructure comprises a long nucleic acid strand hybridized to a plurality of nucleic acid strands that are shorter than the long nucleic acid strand.

25. The nanoparticle of claim 1, wherein the nucleic acid nanostructure comprises a plurality of nucleic acid strands hybridized to each other, each nucleic acid strand having a length of less than 200 nm.

26. The nanoparticle of claim 1, wherein the nanoparticle has a void volume of at least 50%.

27. The nanoparticle of claim 26, wherein the nanoparticle has a void volume of at least 75%.

28. A nanoparticle comprising a nucleic acid nanostructure core and a lipid bilayer coating comprising an interior layer, a transmembrane region, and an exterior layer coating, wherein the nucleic acid nanostructure is attached to a hydrophobic moiety through a single-stranded oligonucleotide conjugate comprising the hydrophobic moiety, wherein the hydrophobic moiety is in contact with the lipid bilayer coating.

29. The nanoparticle of claim 28, wherein the hydrophobic moiety is positioned within the transmembrane region of the lipid bilayer, or extends through the lipid bilayer and is positioned exterior to the nanoparticle.

30. A nanoparticle comprising a nucleic acid nanostructure core and a lipid bilayer coating comprising an interior layer, a transmembrane region, and an exterior layer coating, wherein the nucleic acid nanostructure is attached to a hydrophobic moiety through a binding pair, one member of which is attached to the nanostructure and one member of which is attached to the hydrophobic moiety, wherein the hydrophobic moiety is in contact with the lipid bilayer coating.

31. The nanoparticle of claim 30, wherein the hydrophobic moiety is positioned within the transmembrane region of the lipid bilayer, or extends through the lipid bilayer and is positioned exterior to the nanoparticle.

* * * * *